United States Patent
Nguyen

(10) Patent No.: US 9,701,656 B2
(45) Date of Patent: Jul. 11, 2017

(54) TIOPRONIN PRODRUGS, PHARMACEUTICAL COMPOSITIONS THEREOF, AND METHODS OF USE

(71) Applicant: Mark Quang Nguyen, San Jose, CA (US)

(72) Inventor: Mark Quang Nguyen, San Jose, CA (US)

(73) Assignee: Mark Quang Nguyen, San Jose, CA (US)

( * ) Notice: Subject to any disclaimer, the term of this patent is extended or adjusted under 35 U.S.C. 154(b) by 0 days.

(21) Appl. No.: 14/935,405

(22) Filed: Nov. 7, 2015

(65) Prior Publication Data

US 2017/0129867 A1    May 11, 2017

(51) Int. Cl.
*C07C 329/06* (2006.01)
*C07D 317/40* (2006.01)

(52) U.S. Cl.
CPC .......... *C07D 317/40* (2013.01); *C07C 329/06* (2013.01); *C07C 2101/14* (2013.01)

(58) Field of Classification Search
CPC .. C07D 317/40; C07C 329/06; C07C 2101/14
USPC ....................................................... 514/467
See application file for complete search history.

*Primary Examiner* — Uma Ramachandran

(57) ABSTRACT

Tiopronin prodrugs, pharmaceutical compositions comprising the tiopronin prodrugs, and methods of using tiopronin prodrugs and pharmaceutical compositions thereof for treating liver, kidney, lung, neurological, inflammatory, and autoimmune disorders including non-alcoholic steatohepatitis, Wilson's disease, cystinuria, irritable bowel disorder, ulcerative colitis, rheumatoid arthritis, chronic obstructive pulmonary disease, interstitial lung disease, asthma, cystic fibrosis, Parkinson's disease, and Huntington's disease.

18 Claims, No Drawings

TIOPRONIN PRODRUGS, PHARMACEUTICAL COMPOSITIONS THEREOF, AND METHODS OF USE

FIELD

Disclosed herein are tiopronin prodrugs, and methods of using tiopronin prodrugs and pharmaceutical compositions thereof for treating liver, kidney, lung, neurological, inflammatory, and autoimmune disorders including non-alcoholic steatohepatitis, Wilson's disease, cystinuria, irritable bowel disorder, ulcerative colitis, rheumatoid arthritis, chronic obstructive pulmonary disease, interstitial lung disease, asthma, cystic fibrosis, Parkinson's disease, and Huntington's disease.

BACKGROUND

Tiopronin is approved in United States to treat patients with cystinuria who are not tolerant to D-penicillamine.

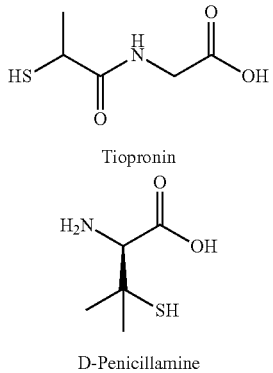

Tiopronin

D-Penicillamine

However, tiopronin exhibits poor oral dosing characteristics. Tiopronin requires a dosing frequency of three times a day and one hour before or two hours after a meal.

SUMMARY

Tiopronin prodrugs having high gastrointestinal permeability and/or absorption and minimal degradation/cleavage in the gut lumen or enterocyte cytoplasm are desirable. Such tiopronin prodrugs, which provide higher oral bioavailability and plasma levels of the parent compound, tiopronin, may: enhance the efficacy/responder rate compared to present tiopronin; facilitate the use of lower doses, reduce dosing frequency, and standardize dosing regimens; reduce food effects; reduce gastrointestinal side effects/toxicity; and reduce interpatient treatment variability.

In a first aspect, compounds of Formula (I) are provided:

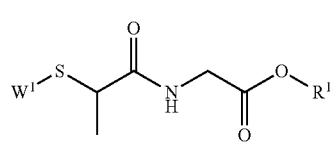

or a pharmaceutically acceptable salt thereof, wherein:

$R^1$ is chosen from hydrogen, $C_{1-6}$ alkyl, $C_{1-6}$ heteroalkyl, $C_{3-12}$ cycloalkyl, $C_{3-12}$ heterocycloalkyl, $C_{5-10}$ aryl, and $C_{5-10}$ heteroaryl; and $W^1$ is chosen from substituents of Formula (I-a) and Formula (I-b):

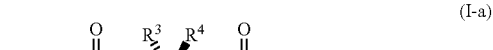

and

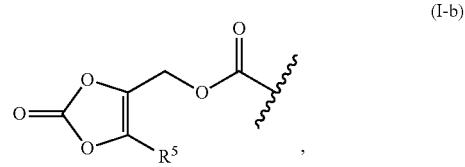

wherein $R^2$, $R^3$, $R^4$, and $R^5$ are independently chosen from hydrogen, $C_{1-6}$ alkyl, $C_{1-6}$ heteroalkyl, $C_{3-12}$ cycloalkyl, $C_{3-12}$ heterocycloalkyl, $C_{5-10}$ aryl, and $C_{5-10}$ heteroaryl; and $Y^1$ is chosen from a bond and —O—.

In a second aspect, pharmaceutical compositions are provided comprising a compound of Formula (I) and at least one pharmaceutically acceptable vehicle.

In a third aspect, methods of treating a disease in a patient are provided comprising administering to a patient in need of such treatment a pharmaceutical composition comprising a therapeutically effective amount of a compound of Formula (I). In certain embodiments, the disease is chosen from a liver disease, a lung disease, a neurodegenerative disease, an inflammatory disease, and an autoimmune disease including, for example, cirrhosis, hepatitis, cystinuria, scleroderma, multiple sclerosis, psoriasis, irritable bowel disorder, ulcerative colitis, arthritis, chronic obstructive pulmonary disease, asthma, Parkinson's disease, Huntington's disease, and amyotrophic lateral sclerosis.

DETAILED DESCRIPTION

Definitions

A dash ("-") that is not between two letters or symbols is used to indicate a point of attachment for a moiety or substituent. For example, —$CONH_2$ is bonded through the carbon atom.

"Alkyl" refers to a saturated or unsaturated, branched, or straight-chain, monovalent hydrocarbon radical derived by the removal of one hydrogen atom from a single carbon atom of a parent alkane, alkene, or alkyne. Examples of alkyl groups include, but are not limited to, methyl; ethyls such as ethanyl, ethenyl, and ethynyl; propyls such as propan-1-yl, propan-2-yl, prop-1-en-1-yl, prop-1-en-2-yl, prop-2-en-1-yl(allyl), prop-1-yn-1-yl, prop-2-yn-1-yl, etc.; butyls such as butan-1-yl, butan-2-yl, 2-methyl-propan-1-yl, 2-methyl-propan-2-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, but-1-yn-1-yl, but-1-yn-3-yl, but-3-yn-1-yl, etc.; and the like.

The term "alkyl" is specifically intended to include groups having any degree or level of saturation, i.e., groups having exclusively single carbon-carbon bonds, groups having one or more double carbon-carbon bonds, groups having one or more triple carbon-carbon bonds, and groups having combinations of single, double, and triple carbon-carbon bonds. Where a specific level of saturation is intended, the terms alkanyl, alkenyl, and alkynyl are used. In certain embodiments, an alkyl group can have from 1 to 20 carbon atoms ($C_{1-20}$) in certain embodiments, from 1 to 10 carbon atoms ($C_{1-10}$), in certain embodiments from 1 to 8 carbon atoms ($C_{1-8}$), in certain embodiments, from 1 to 6 carbon atoms ($C_{1-6}$), in certain embodiments from 1 to 4 carbon atoms ($C_{1-4}$), and in certain embodiments, from 1 to 3 carbon atoms ($C_{1-3}$).

"Aryl" refers to a monovalent aromatic hydrocarbon radical derived by the removal of one hydrogen atom from a single carbon atom of a parent aromatic ring system. Aryl benzene; bicyclic ring systems wherein at least one ring is carbocyclic and aromatic, for example, naphthalene, indane, and tetralin; and tricyclic ring systems wherein at least one ring is carbocyclic and aromatic, for example, fluorene. Aryl encompasses multiple ring systems having at least one carbocyclic aromatic ring fused to at least one carbocyclic aromatic ring, cycloalkyl ring, or heterocycloalkyl ring. For example, aryl includes a phenyl ring fused to a 5- to 7-membered heterocycloalkyl ring containing one or more heteroatoms chosen from N, O, and S. For such fused, bicyclic ring systems wherein only one of the rings is a carbocyclic aromatic ring, the radical carbon atom may be at the carbocyclic aromatic ring or at the heterocycloalkyl ring. Examples of aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like. In certain embodiments, an aryl group can have from 6 to 20 carbon atoms ($C_{6-20}$), from 6 to 12 carbon atoms ($C_{6-12}$), from 6 to 10 carbon atoms ($C_{6-10}$), and in certain embodiments from 6 to 8 carbon atoms ($C_{6-8}$). Aryl, however, does not encompass or overlap in any way with heteroaryl, separately defined herein.

"Compounds" of Formula (I) disclosed herein include any specific compounds within the formula. Compounds may be identified either by their chemical structure and/or chemical name. Compounds are named using Accelrys Draw 4.1 SP1, version MDL.Draw.Editor 4.1. 100.70 (Accelrys, Inc., San Diego, Calif.). When the chemical structure and chemical name conflict, the chemical structure is determinative of the identity of the compound. The compounds described herein may comprise one or more chiral centers and/or double bonds and therefore may exist as stereoisomers such as double-bond isomers (i.e., geometric isomers), enantiomers, or diastereomers. Accordingly, any chemical structures within the scope of the specification depicted, in whole or in part, with a relative configuration encompass all possible enantiomers and stereoisomers of the illustrated compounds including the stereoisomerically pure form (e.g., geometrically pure, enantiomerically pure, or diastereomerically pure) and enantiomeric and stereoisomeric mixtures. Enantiomeric and stereoisomeric mixtures may be resolved into their component enantiomers or stereoisomers using separation techniques or chiral synthesis techniques well known to the skilled artisan. Compounds of Formula (I) include, but are not limited to, optical isomers of compounds of Formula (I), racemates thereof, and other mixtures thereof. In such embodiments, a single enantiomer or diastereomer, i.e., optically active form can be obtained by asymmetric synthesis or by resolution of the racemates. Resolution of the racemates may be accomplished, for example, by conventional methods such as crystallization in the presence of a resolving agent, or chromatography using, for example, chiral stationary phases. Not withstanding the foregoing, in compounds of Formula (I) the configuration of the illustrated double bond is only in the E configuration (i.e. trans configuration).

Compounds of Formula (I) may also exist in several tautomeric forms including the enol form, the keto form, and mixtures thereof. Accordingly, the chemical structures depicted herein encompass all possible tautomeric forms of the illustrated compounds. Compounds of Formula (I) also include isotopically labeled compounds where one or more atoms have an atomic mass different from the atomic mass conventionally found in nature. Examples of isotopes that may be incorporated into the compounds disclosed herein include, but are not limited to, $^2$H, $^3$H, $^{11}$C $^{13}$C, $^{14}$C, $^{15}$N, $^{18}$O, $^{17}$O, etc. Compounds may exist in unsolvated forms as well as solvated forms, including hydrated forms and as N-oxides. In general, compounds as referred to herein may be free acid, hydrated, solvated, or N-oxides. Certain compounds may exist in multiple crystalline, co-crystalline, or amorphous forms. Compounds of Formula (I) include pharmaceutically acceptable salts thereof, or pharmaceutically acceptable solvates of the free acid form of any of the foregoing, as well as crystalline forms of any of the foregoing.

Compounds of Formula (I) also include solvates. A solvate refers to a molecular complex of a compound with one or more solvent molecules in a stoichiometric or non-stoichiometric amount. Such solvent molecules are those commonly used in the pharmaceutical art, which are known to be innocuous to a patient, e.g., water, ethanol, and the like. A molecular complex of a compound or moiety of a compound and a solvent can be stabilized by non-covalent intra-molecular forces such as, for example, electrostatic forces, van der Waals forces, or hydrogen bonds. The term "hydrate" refers to a solvate in which the one or more solvent molecules is water.

Further, when partial structures of the compounds are illustrated, an asterisk (*) or a wavy line ( ~~~~ ) indicates the point of attachment of the partial structure to the rest of the molecule.

"Cycloalkyl" refers to a saturated or partially unsaturated cyclic alkyl radical. Where a specific level of saturation is intended, the nomenclature cycloalkanyl or cycloalkenyl is used. Examples of cycloalkyl groups include, but are not limited to, groups derived from cyclopropane, cyclobutane, cyclopentane, cyclohexane, and the like. In certain embodiments, a cycloalkyl group is $C_{3-15}$ cycloalkyl, $C_{3-12}$ cycloalkyl, and in certain embodiments, $C_{3-8}$ cycloalkyl.

"Disease" refers to a disease, disorder, condition, or symptom of any of the foregoing.

"Drug" as defined under 21 U.S.C. §321(g)(1) means "(A) articles recognized in the official United States Pharmacopoeia, official Homeopathic Pharmacopoeia of the United States, or official National Formulary, or any supplement to any of them; and (B) articles intended for use in the diagnosis, cure, mitigation, treatment, or prevention of disease in man or other animals; and (C) articles (other than food) intended to affect the structure or any function of the body of man or other animals . . . ."

"Halogen" refers to a fluoro, chloro, bromo, or iodo group. In certain embodiments, halogen refers to a chloro group.

"Heteroalkyl" by itself or as part of another substituent refers to an alkyl group in which one or more of the carbon atoms (and certain associated hydrogen atoms) are independently replaced with the same or different heteroatomic groups. Examples of heteroatomic groups include, but are not limited to, —O—, —S—, —O—O—, —S—S—, —O—S—, —NR$^{91}$—, =N—N=, —N=N—, —N=N—NR$^{91}$—, —PR$^{91}$—, —P(O)$_2$—, —POR$^{91}$—, —O—P(O)$_2$—, —SO—, —SO$_2$—, —Sn(R$^{91}$)$_2$—, and the like, where each R$^{91}$ is independently chosen from hydrogen, C$_{1-6}$ alkyl, substituted C$_{1-6}$ alkyl, C$_{6-12}$ aryl, substituted C$_{6-12}$ aryl, C$_{7-18}$ arylalkyl, substituted C$_{7-18}$ arylalkyl, C$_{3-7}$ cycloalkyl, substituted C$_{3-7}$ cycloalkyl, C$_{3-7}$ heterocycloalkyl, substituted C$_{3-7}$ heterocycloalkyl, C$_{1-6}$ heteroalkyl, substituted C$_{1-6}$ heteroalkyl, C$_{6-12}$ heteroaryl, substituted C$_{6-12}$ heteroaryl, C$_{7-18}$ heteroarylalkyl, or substituted C$_{7-18}$ heteroarylalkyl. Reference to, for example, a C$_{1-6}$ heteroalkyl, means a C$_{1-6}$ alkyl group in which at least one of the carbon atoms (and certain associated hydrogen atoms) is replaced with a heteroatom. For example C$_{1-6}$ heteroalkyl includes groups having five carbon atoms and one heteroatom, groups having four carbon atoms and two heteroatoms, etc. In certain embodiments, each R$^{91}$ is independently chosen from hydrogen and C$_{1-3}$ alkyl. In certain embodiments, a heteroatomic group is chosen from —O—, —S—, —NH—, —N(CH$_3$)—, and —SO$_2$—; and in certain embodiments, the heteroatomic group is —O—.

"Heteroaryl" by itself or as part of another substituent refers to a aryl group in which one or more of the carbon atoms (and certain associated hydrogen atoms) are independently replaced with the same or different heteroatomic groups. Examples of heteroatomic groups include, but are not limited to, —O—, —S—, —O—O—, —S—S—, —O—S—, —NR$^{91}$—, =N—N=, —N=N—, —N=N—NR$^{91}$—, —PR$^{91}$—, —P(O)$_2$—, —POR$^{91}$—, —O—P(O)$_2$—, —SO—, —SO$_2$—, —Sn(R$^{91}$)$_2$—, and the like, where each R$^{91}$ is independently chosen from hydrogen, C$_{1-6}$ alkyl, substituted C$_{1-6}$ alkyl, C$_{6-12}$ aryl, substituted C$_{6-12}$ aryl, C$_{7-18}$ arylalkyl, substituted C$_{7-18}$ arylalkyl, C$_{3-7}$ cycloalkyl, substituted C$_{3-7}$ cycloalkyl, C$_{3-7}$ heterocycloalkyl, substituted C$_{3-7}$ heterocycloalkyl, C$_{1-6}$ heteroalkyl, substituted C$_{1-6}$ heteroalkyl, C$_{6-12}$ heteroaryl, substituted C$_{6-12}$ heteroaryl, C$_{7-18}$ heteroarylalkyl, or substituted C$_{7-18}$ heteroarylalkyl.

Heteroaryl encompasses multiple ring systems having at least one heteroaromatic ring fused to at least one other ring, which can be aromatic or non-aromatic. For example, heteroaryl encompasses bicyclic rings in which one ring is heteroaromatic and the second ring is a heterocycloalkyl ring. For such fused, bicyclic heteroaryl ring systems wherein only one of the rings contains one or more heteroatoms, the radical carbon may be at the aromatic ring or at the heterocycloalkyl ring.

Examples of heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, thiazolidine, oxazolidine, and the like. In certain embodiments, a heteroaryl group is from 4- to 20-membered heteroaryl (C$_{4-20}$), and in certain embodiments from 4- to 12-membered heteroaryl (C$_{4-10}$). In certain embodiments, heteroaryl groups are those derived from thiophene, pyrrole, benzothiophene, benzofuran, indole, pyridine, quinoline, imidazole, oxazole, or pyrazine. For example, in certain embodiments, C$_5$ heteroaryl can be furyl, thienyl, pyrrolyl, imidazolyl, pyrazolyl, isothiazolyl, and isoxazolyl.

"Heterocycloalkyl" by itself or as part of another substituent refers to a cycloalkyl group in which one or more of the carbon atoms (and certain associated hydrogen atoms) are independently replaced with the same or different heteroatomic groups. Examples of heteroatomic groups include, but are not limited to, —O—, —S—, —O—O—, —S—S—, —O—S—, —NR$^{91}$—, =N—N=, —N=N—, —N=N—NR$^{91}$—, —PR$^{91}$—, —P(O)$_2$—, —POR$^{91}$—, —O—P(O)$_2$—, —SO—, —SO$_2$—, —Sn(R$^{91}$)$_2$—, and the like, where each R$^{91}$ is independently chosen from hydrogen, C$_{1-6}$ alkyl, substituted C$_{1-6}$ alkyl, C$_{6-12}$ aryl, substituted C$_{6-12}$ aryl, C$_{7-18}$ arylalkyl, substituted C$_{7-18}$ arylalkyl, C$_{3-7}$ cycloalkyl, substituted C$_{3-7}$ cycloalkyl, C$_{3-7}$ heterocycloalkyl, substituted C$_{3-7}$ heterocycloalkyl, C$_{1-6}$ heteroalkyl, substituted C$_{1-6}$ heteroalkyl, C$_{6-12}$ heteroaryl, substituted C$_{6-12}$ heteroaryl, C$_{7-18}$ heteroarylalkyl, or substituted C$_{7-18}$ heteroarylalkyl. Reference to, for example, a C$_{3-6}$ heterocycloalkyl, means a C$_{3-6}$ cycloalkyl group in which at least one of the carbon atoms (and certain associated hydrogen atoms) is replaced with a heteroatom. For example C$_{3-6}$ heterocycloalkyl includes groups having five carbon atoms and one heteroatom, groups having four carbon atoms and two heteroatoms, etc. In certain embodiments, each R$^{91}$ is independently chosen from hydrogen and C$_{1-3}$ alkyl. In certain embodiments, a heteroatomic group is chosen from —O—, —S—, —NH—, —N(CH$_3$)—, and —SO$_2$—; and in certain embodiments, the heteroatomic group is —O—.

"Parent aromatic ring system" refers to an unsaturated cyclic or polycyclic ring system having a conjugated π (pi) electron system. Included within the definition of "parent aromatic ring system" are fused ring systems in which one or more of the rings are aromatic and one or more of the rings are saturated or unsaturated, such as, for example, fluorene, indane, indene, phenalene, etc. Examples of parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like.

"Parent heteroaromatic ring system" refers to an aromatic ring system in which one or more carbon atoms (and any associated hydrogen atoms) are independently replaced with the same or different heteroatom in such a way as to maintain the continuous π-electron system characteristic of aromatic systems and a number of out-of-plane π-electrons corresponding to the Hückel rule (4n+2). Examples of heteroatoms to replace the carbon atoms include, but are not limited to, N, P, O, S, and Si, etc. Specifically included within the definition of "parent heteroaromatic ring systems" are fused ring systems in which one or more of the rings are aromatic and one or more of the rings are saturated or unsaturated, such as, for example, arsindole, benzodioxan, benzofuran, chromane, chromene, indole, indoline, xanthene, etc. Examples of parent heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, thiazolidine, oxazolidine, and the like.

"Patient" refers to a mammal, for example, a human.

"Pharmaceutically acceptable" refers to approved or approvable by a regulatory agency of the Federal or a state government or listed in the U.S. Pharmacopoeia or other generally recognized pharmacopoeia for use in animals, and more particularly in humans.

"Pharmaceutically acceptable salt" refers to a salt of a compound, which possesses the desired pharmacological activity of the parent compound. Such salts include acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; and salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine, and the like. In certain embodiments, a pharmaceutically acceptable salt is the hydrochloride salt. In certain embodiments, a pharmaceutically acceptable salt is the sodium salt.

"Pharmaceutically acceptable vehicle" refers to a pharmaceutically acceptable diluent, a pharmaceutically acceptable adjuvant, a pharmaceutically acceptable excipient, a pharmaceutically acceptable carrier, or a combination of any of the foregoing with which a compound provided by the present disclosure may be administered to a patient and which does not destroy the pharmacological activity thereof and which is non-toxic when administered in doses sufficient to provide a therapeutically effective amount of the compound.

"Pharmaceutical composition" refers to a compound of Formula (I) and at least one pharmaceutically acceptable vehicle, with which the compound of Formula (I) is administered to a patient.

"Substituted" refers to a group in which one or more hydrogen atoms are independently replaced with the same or substituent group(s). In certain embodiments, each substituent group is independently chosen from halogen, —OH, —CN, —CF$_3$, =O, —NO$_2$, benzyl, —C(O)NR$^{21}_2$, —R$^{21}$, —OR$^{21}$, —C(O)R$^{21}$, —COOR$^{21}$, —C(R$^{21}$)NH$_2$, —C(O)C(R$^{21}$)NH$_2$, —C(R$^{21}$)C(O)OH, —NC(R$^{21}$)C(O)OH, —NR$^{21}_2$, —NR$^{21}$C(O)R$^{21}$, and —O(O)R$^{21}$, wherein each R$^{21}$ is independently chosen from hydrogen, C$_{1-6}$ alkyl, C$_{1-6}$ heteroalkyl, C$_{3-12}$ cycloalkyl, C$_{5-10}$ aryl, and C$_{5-10}$ heteroaryl. In certain embodiments, each substituent group is independently chosen from halogen, —OH, —CN, —CF$_3$, =O, —NO$_2$, benzyl, —C(O)NR$^{21}_2$, —R$^{21}$, —OR$^{21}$, —C(O)R$^{21}$, —COOR$^{21}$, —C(R$^{21}$)NH$_2$, —C(O)C(R$^{21}$)NH$_2$, —C(R$^{21}$)C(O)OH, —NC(R$^{21}$)C(O)OH, —NR$^{21}_2$, —NR$^{21}$C(O)R$^{21}$, and —O(O)R$^{21}$, wherein each R$^{21}$ is independently chosen from hydrogen, C$_{1-6}$ alkyl, C$_{1-6}$ heteroalkyl, C$_{3-12}$ cycloalkyl, C$_{5-10}$ aryl, and C$_{5-10}$ heteroaryl. In certain embodiments, each substituent group is independently chosen from —OH, —NH$_2$, and C$_{1-4}$ alkyl. In certain embodiments, each substituent group is independently chosen from —OH, —C(O)NR$^{21}_2$, —R$^{21}$, —C(O)R$^{21}$, —COOR$^{21}$, —C(R$^{21}$)NH$_2$, —C(O)C(R$^{21}$)NH$_2$—C(R$^{21}$)C(O)OH, and —NC(R$^{21}$)C(O)OH, wherein each R$^{21}$ is independently chosen from a hydrogen, methyl, isopropyl, sec-butyl, phenyl, benzyl, p-hydroxybenzyl, 1H-imidazol-5-ylmethyl, 1H-indol-3-ylmethyl, —CH$_2$OH, —CH(OH)CH$_3$, —CH$_2$CH$_2$SCH$_3$, —CH$_2$CONH$_2$, —CH$_2$COOH, —CH$_2$CH$_2$CONH$_2$, —CH$_2$CH$_2$COOH, —(CH$_2$)$_3$NHC(=NH)NH$_2$, —(CH$_2$)$_3$NH$_2$, —(CH$_2$)$_3$NHCOCH$_3$, —(CH$_2$)$_3$NHCHO, —(CH$_2$)$_4$NHC(=NH)NH$_2$, —(CH$_2$)$_4$NH$_2$, —(CH$_2$)$_4$NHCOCH$_3$, —(CH$_2$)$_4$NHCHO, —(CH$_2$)$_3$NHCONH$_2$, —(CH$_2$)$_4$NHCONH$_2$, and —CH$_2$CH$_2$CH(OH)CH$_2$NH$_2$.

"Treating" or "treatment" of any disease refers to reversing, alleviating, arresting, or ameliorating a disease or at least one of the clinical symptoms of a disease, reducing the risk of acquiring a disease or at least one of the clinical symptoms of a disease, inhibiting the progress of a disease or at least one of the clinical symptoms of the disease or reducing the risk of developing a disease or at least one of the clinical symptoms of a disease. "Treating" or "treatment" also refers to inhibiting the disease, either physically, (e.g., stabilization of a discernible symptom), physiologically, (e.g., stabilization of a physical parameter), or both, and to inhibiting at least one physical parameter that may or may not be discernible to the patient. In certain embodiments, "treating" or "treatment" refers to delaying the onset of the disease or at least one or more symptoms thereof in a patient which may be exposed to or predisposed to a disease even though that patient does not yet experience or display symptoms of the disease.

"Therapeutically effective amount" refers to the amount of a compound that, when administered to a subject for treating a disease, or at least one of the clinical symptoms of a disease, is sufficient to affect such treatment of the disease or symptom thereof. The "therapeutically effective amount" may vary depending, for example, on the compound, the disease and/or symptoms of the disease, severity of the disease and/or symptoms of the disease or disorder, the age, weight, and/or health of the patient to be treated, and the judgment of the prescribing physician. An appropriate amount in any given instance may be ascertained by those skilled in the art or capable of determination by routine experimentation.

"Therapeutically effective dose" refers to a dose that provides effective treatment of a disease or disorder in a patient. A therapeutically effective dose may vary from compound to compound, and from patient to patient, and may depend upon factors such as the condition of the patient and the route of delivery. A therapeutically effective dose may be determined in accordance with routine pharmacological procedures known to those skilled in the art.

Reference is now made in detail to certain embodiments of compounds, compositions, and methods. The disclosed embodiments are not intended to be limiting of the claims. To the contrary, the claims are intended to cover all alternatives, modifications, and equivalents.

Compounds

In a first aspect, compounds of Formula (I) are provided:

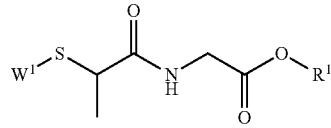
(I)

or a pharmaceutically acceptable salt thereof, wherein:

$R^1$ is chosen from hydrogen, $C_{1-6}$ alkyl, $C_{1-6}$ heteroalkyl, $C_{3-12}$ cycloalkyl, $C_{3-12}$ heterocycloalkyl, $C_{5-10}$ aryl, and $C_{5-10}$ heteroaryl; and $W^1$ is chosen from substituents of Formula (I-a) and Formula (I-b):

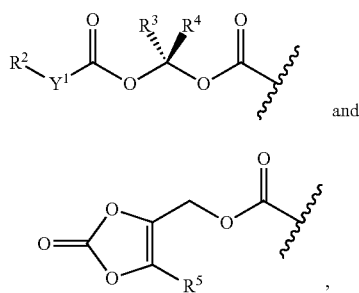
(I-a)

and (I-b)

wherein $R^2$, $R^3$, $R^4$, and $R^5$ are independently chosen from hydrogen, $C_{1-6}$ alkyl, $C_{1-6}$ heteroalkyl, $C_{3-12}$ cycloalkyl, $C_{3-12}$ heterocycloalkyl, $C_{5-10}$ aryl, and $C_{5-10}$ heteroaryl; and $Y^1$ is chosen from a bond and —O—.

In certain embodiments of a compound of Formula (I), $R^1$, $R^2$, $R^3$, $R^4$, and $R^5$ are independently chosen from hydrogen, $C_{1-6}$ alkyl, $C_{1-6}$ heteroalkyl, $C_{3-12}$ cycloalkyl, $C_{3-12}$ heterocycloalkyl, $C_{5-10}$ aryl, and $C_{5-10}$ heteroaryl.

In certain embodiments of a compound of Formula (I), $R^1$, $R^2$, $R^3$, $R^4$, and $R^5$ are independently chosen from hydrogen and $C_{1-6}$ alkyl.

In certain embodiments of a compound of Formula (I), $R^1$, $R^2$, $R^3$, $R^4$, and $R^5$ are independently chosen from hydrogen, methyl, ethyl, n-propyl, isopropyl, n-butyl, isobutyl, tert-butyl, n-pentyl, pentyl-2-yl, 2-methylbutyl, isopentyl, 3-methylbutan-2-yl, neopentyl, tert-pentyl, n-hexyl, hexan-2-yl, 2-methylpentyl, 3-methylpentyl, 4-methylpentyl, 3-methylpentan-2-yl, 4-methylpentan-2-yl, 2,3-dimethylbutyl, and 3,3-dimethylbutyl.

In certain embodiments of a compound of Formula (I), $R^1$, $R^2$, $R^3$, $R^4$, and $R^5$ are independently chosen from hydrogen and $C_{1-6}$ heteroalkyl.

In certain embodiments of a compound of Formula (I), $R^1$, $R^2$, $R^3$, $R^4$, and $R^5$ are independently chosen from hydrogen, methoxymethyl, 2-methoxyethyl, 2-ethoxyethyl, 3-methoxypropyl, 3-ethoxypropyl, and 4-methoxybutyl.

In certain embodiments of a compound of Formula (I), $R^1$, $R^2$, $R^3$, $R^4$, and $R^5$ are independently chosen from hydrogen and $C_{3-12}$ cycloalkyl.

In certain embodiments of a compound of Formula (I), $R^1$, $R^2$, $R^3$, $R^4$, and $R^5$ are independently chosen from hydrogen, cyclopropyl, cyclobutyl, cyclopentyl, cyclohexyl, cycloheptyl, and cyclooctyl.

In certain embodiments of a compound of Formula (I), $R^1$, $R^2$, $R^3$, $R^4$, and $R^5$ are independently chosen from hydrogen and $C_{3-12}$ heterocycloalkyl.

In certain embodiments of a compound of Formula (I), $R^1$, $R^2$, $R^3$, $R^4$, and $R^5$ are independently chosen from hydrogen; azepan-1-yl; azetidin-1-yl; 2H-azet-1-yl; aziridin-1-yl; azirin-1-yl; azocan-1-yl; 1,2-dihydroimidazol-3-yl; 2,4-dihydroimidazol-3-yl; 4,5-dihydroimidazol-1-yl; 1,3-dihydropyrazol-2-yl; 1,5-dihydropyrazol-2-yl; 3,4-dihydropyrazol-2-yl; 2,3-dihydropyrrol-1-yl; 2,5-dihydropyrrol-1-yl; 1,5-dihydro-1,2,4-triazol-4-yl; 3,5-dihydro-1,2,4-triazol-4-yl; 4,5-dihydrotriazol-1-yl; 1,3,5-dioxazinan-5-yl; 1,3,2-dioxazol-2-yl; hexahydropyrimidin-1-yl; imidazolidin-1-yl; morpholin-4-yl; 1,3-oxazetidin-3-yl; oxazetidin-2-yl; 1,3-oxazinan-3-yl; oxazolidin-3-yl; 2H-oxazol-3-yl; piperazin-1-yl; 1-piperidyl; pyrazolidin-1-yl; and pyrrolidin-1-yl.

In certain embodiments of a compound of Formula (I), $R^1$, $R^2$, $R^3$, $R^4$, and $R^5$ are independently chosen from hydrogen, morpholin-4-yl; oxazolidin-3-yl; 1-piperidyl; pyrrolidin-1-yl; 2,5-dioxopyrrolidin-1-yl; and 2-oxopyrrolidin-1-yl.

In certain embodiments of a compound of Formula (I), $R^1$, $R^2$, $R^3$, $R^4$, and $R^5$ are independently chosen from hydrogen and morpholin-4-yl.

In certain embodiments of a compound of Formula (I), $R^1$, $R^2$, $R^3$, $R^4$, and $R^5$ are independently chosen from hydrogen and $C_{5-10}$ aryl.

In certain embodiments of a compound of Formula (I), $R^1$, $R^2$, $R^3$, $R^4$, and $R^5$ are independently chosen from hydrogen, phenyl, benzyl, phenylphenyl, and naphthyl.

In certain embodiments of a compound of Formula (I), $R^1$, $R^2$, $R^3$, $R^4$, and $R^5$ are independently chosen from hydrogen and $C_{5-10}$ heteroaryl.

In certain embodiments of a compound of Formula (I), $R^1$, $R^2$, $R^3$, $R^4$, and $R^5$ are independently chosen from hydrogen; furyl; imidazol-yl; indol-yl; isoxazol-yl; oxazol-yl; pyrazin-yl; pyridyl; pyrimidin-yl; pyrrol-yl; tetrazol-yl; thienyl; and triazol-yl.

In certain embodiments of a compound of Formula (I), $R^1$, $R^2$, $R^3$, $R^4$, and $R^5$ are independently chosen from hydrogen; 2-furyl; 3-furyl; 1H-imidazol-2-yl; 1H-imidazol-4-yl; 1H-indol-2-yl; 1H-indol-3-yl; 1H-indol-4-yl; 1H-indol-5-yl; 1H-indol-6-yl; 1H-indol-7-yl; isoxazol-3-yl; isoxazol-4-yl; isoxazol-5-yl; oxazol-2-yl; oxazol-4-yl; oxazol-5-yl; pyrazin-2-yl; 2-pyridyl; 3-pyridyl; 4-pyridyl; pyrimidin-2-yl; pyrimidin-4-yl; pyrimidin-5-yl; 1H-pyrrol-2-yl; 1H-pyrrol-3-yl; 2H-pyrrol-2-yl; 2H-pyrrol-3-yl; 1H-tetrazol-5-yl; 2-thienyl; 3-thienyl; 1H-triazol-4-yl; and 4H-1,2,4-triazol-3-yl.

In certain embodiments of a compound of Formula (I), $R^1$, $R^2$, $R^3$, $R^4$, and $R^5$ are independently chosen from hydrogen; benzimidazol-1-yl; benzotriazol-1-yl; 1,2,4-benzoxadiazin-2-yl; 1,4-benzoxazin-4-yl; carbazol-9-yl; imidazol-1-yl; indazol-1-yl; indolin-1-yl; indol-1-yl; isoindolin-2-yl; phenoxazin-10-yl; purin-7-yl; purin-9-yl; pyrazol-1-yl; pyrrol-1-yl; tetrazol-1-yl; triazol-1-yl; and 1,2,4-triazol-4-yl.

In certain embodiments of a compound of Formula (I), $W^1$ is chosen from substituents of Formula (I-a) and Formula (I-b).

In certain embodiments of a compound of Formula (I), $W^1$ is the substituent of Formula (I-a), wherein $R^2$, $R^3$, and $R^4$ are independently chosen from hydrogen, methyl, ethyl, isopropyl, tert-butyl, cyclohexyl, phenyl, and benzyl; and $Y^1$ is chosen from a bond and —O—.

In certain embodiments of a compound of Formula (I), $W^1$ is the substituent of Formula (I-a), wherein $R^2$, $R^3$, and $R^4$ are independently chosen from hydrogen, methyl, ethyl, isopropyl, tert-butyl, cyclohexyl, phenyl, and benzyl; and $Y^1$ is a bond.

In certain embodiments of a compound of Formula (I), $W^1$ is the substituent of Formula (I-a), wherein $R^2$ is chosen from methyl, ethyl, isopropyl, tert-butyl, cyclohexyl, phenyl, and benzyl; $R^3$ and $R^4$ are chosen from hydrogen and methyl; and $Y^1$ is a bond.

In certain embodiments of a compound of Formula (I), $W^1$ is the substituent of Formula (I-a), wherein $R^2$ is chosen from methyl, ethyl, isopropyl, tert-butyl, cyclohexyl, phenyl, and benzyl; $R^3$ and $R^4$ are hydrogen; and $Y^1$ is a bond.

In certain embodiments of a compound of Formula (I), $W^1$ is the substituent of Formula (I-a), wherein $R^2$ is methyl, $R^3$ and $R^4$ are hydrogen, and $Y^1$ is a bond.

In certain embodiments of a compound of Formula (I), $W^1$ is the substituent of Formula (I-a), wherein $R^2$ is ethyl, $R^3$ and $R^4$ are hydrogen, and $Y^1$ is a bond.

In certain embodiments of a compound of Formula (I), $W^1$ is the substituent of Formula (I-a), wherein $R^2$ is isopropyl, $R^3$ and $R^4$ are hydrogen, and $Y^1$ is a bond.

In certain embodiments of a compound of Formula (I), $W^1$ is the substituent of Formula (I-a), wherein $R^2$ is tert-butyl, $R^3$ and $R^4$ are hydrogen, and $Y^1$ is a bond.

In certain embodiments of a compound of Formula (I), $W^1$ is the substituent of Formula (I-a), wherein $R^2$ is cyclohexyl, $R^3$ and $R^4$ are hydrogen, and $Y^1$ is a bond.

In certain embodiments of a compound of Formula (I), $W^1$ is the substituent of Formula (I-a), wherein $R^2$ is phenyl, $R^3$ and $R^4$ are hydrogen, and $Y^1$ is a bond.

In certain embodiments of a compound of Formula (I), $W^1$ is the substituent of Formula (I-a), wherein $R^2$ is benzyl, $R^3$ and $R^4$ are hydrogen, and $Y^1$ is a bond.

In certain embodiments of a compound of Formula (I), $W^1$ is the substituent of Formula (I-b), wherein $R^5$ is chosen from methyl, ethyl, isopropyl, tert-butyl, cyclohexyl, phenyl, and benzyl.

In certain embodiments of a compound of Formula (I), $W^1$ is the substituent of Formula (I-b), wherein $R^5$ is methyl.

In certain embodiments of a compound of Formula (I), $W^1$ is the substituent of Formula (I-b), wherein $R^5$ is phenyl.

In certain embodiments of a compound of Formula (I), $R^1$ is chosen from hydrogen, methyl, ethyl, n-propyl, isopropyl, tert-butyl, cyclohexyl, phenyl, and benzyl; and $W^1$ is chosen from the substituent of Formula (I-a) and Formula (I-b).

In certain embodiments of a compound of Formula (I), $R^1$ is chosen from hydrogen, methyl, ethyl, n-propyl, isopropyl, tert-butyl, cyclohexyl, phenyl, and benzyl; and $W^1$ is chosen from the substituent of Formula (I-a).

In certain embodiments of a compound of Formula (I), $R^1$ is hydrogen; and $W^1$ is the substituent of Formula (I-a), wherein $R^2$ is methyl, $R^3$ and $R^4$ are hydrogen, and $Y^1$ is a bond.

In certain embodiments of a compound of Formula (I), $R^1$ is hydrogen; and $W^1$ is the substituent of Formula (I-a), wherein $R^2$ is ethyl, $R^3$ and $R^4$ are hydrogen, and $Y^1$ is a bond.

In certain embodiments of a compound of Formula (I), $R^1$ is hydrogen; and $W^1$ is the substituent of Formula (I-a), wherein $R^2$ is isopropyl, $R^3$ and $R^4$ are hydrogen, and $Y^1$ is a bond.

In certain embodiments of a compound of Formula (I), $R^1$ is hydrogen; and $W^1$ is the substituent of Formula (I-a), wherein $R^2$ is tert-butyl, $R^3$ and $R^4$ are hydrogen, and $Y^1$ is a bond.

In certain embodiments of a compound of Formula (I), $R^1$ is hydrogen; and $W^1$ is the substituent of Formula (I-a), wherein $R^2$ is cyclohexyl, $R^3$ and $R^4$ are hydrogen, and $Y^1$ is a bond.

In certain embodiments of a compound of Formula (I), $R^1$ is hydrogen; and $W^1$ is the substituent of Formula (I-a), wherein $R^2$ is phenyl, $R^3$ and $R^4$ are hydrogen, and $Y^1$ is a bond.

In certain embodiments of a compound of Formula (I), $R^1$ is hydrogen; and $W^1$ is the substituent of Formula (I-a), wherein $R^2$ is benzyl, $R^3$ and $R^4$ are hydrogen, and $Y^1$ is a bond.

In certain embodiments of a compound of Formula (I), $R^1$ is hydrogen; and $W^1$ is the substituent of Formula (I-a), wherein $R^2$ is methyl, $R^3$ is hydrogen, $R^4$ is methyl, and $Y^1$ is a bond.

In certain embodiments of a compound of Formula (I), $R^1$ is hydrogen; and $W^1$ is the substituent of Formula (I-a), wherein $R^2$ is ethyl, $R^3$ is hydrogen, $R^4$ is methyl, and $Y^1$ is a bond.

In certain embodiments of a compound of Formula (I), $R^1$ is hydrogen; and $W^1$ is the substituent of Formula (I-a), wherein $R^2$ is isopropyl, $R^3$ is hydrogen, $R^4$ is methyl, and $Y^1$ is a bond.

In certain embodiments of a compound of Formula (I), $R^1$ is hydrogen; and $W^1$ is the substituent of Formula (I-a), wherein $R^2$ is tert-butyl, $R^3$ is hydrogen, $R^4$ is methyl, and $Y^1$ is a bond.

In certain embodiments of a compound of Formula (I), $R^1$ is hydrogen; and $W^1$ is the substituent of Formula (I-a), wherein $R^2$ is cyclohexyl, $R^3$ is hydrogen, $R^4$ is methyl, and $Y^1$ is a bond.

In certain embodiments of a compound of Formula (I), $R^1$ is hydrogen; and $W^1$ is the substituent of Formula (I-a), wherein $R^2$ is phenyl, $R^3$ is hydrogen, $R^4$ is methyl, and $Y^1$ is a bond.

In certain embodiments of a compound of Formula (I), $R^1$ is hydrogen; and $W^1$ is the substituent of Formula (I-a), wherein $R^2$ is benzyl, $R^3$ is hydrogen, $R^4$ is methyl, and $Y^1$ is a bond.

In certain embodiments of a compound of Formula (I), $R^1$ is hydrogen; and $W^1$ is the substituent of Formula (I-a), wherein $R^2$ is methyl, $R^3$ is methyl, $R^4$ is hydrogen, and $Y^1$ is a bond.

In certain embodiments of a compound of Formula (I), $R^1$ is hydrogen; and $W^1$ is the substituent of Formula (I-a), wherein $R^2$ is ethyl, $R^3$ is methyl, $R^4$ is hydrogen, and $Y^1$ is a bond.

In certain embodiments of a compound of Formula (I), $R^1$ is hydrogen; and $W^1$ is the substituent of Formula (I-a), wherein $R^2$ is isopropyl, $R^3$ is methyl, $R^4$ is hydrogen, and $Y^1$ is a bond.

In certain embodiments of a compound of Formula (I), $R^1$ is hydrogen; and $W^1$ is the substituent of Formula (I-a), wherein $R^2$ is tert-butyl, $R^3$ is methyl, $R^4$ is hydrogen, and $Y^1$ is a bond.

In certain embodiments of a compound of Formula (I), $R^1$ is hydrogen; and $W^1$ is the substituent of Formula (I-a), wherein $R^2$ is cyclohexyl, $R^3$ is methyl, $R^4$ is hydrogen, and $Y^1$ is a bond.

In certain embodiments of a compound of Formula (I), $R^1$ is hydrogen; and $W^1$ is the substituent of Formula (I-a), wherein $R^2$ is phenyl, $R^3$ is methyl, $R^4$ is hydrogen, and $Y^1$ is a bond.

In certain embodiments of a compound of Formula (I), $R^1$ is hydrogen; and $W^1$ is the substituent of Formula (I-a), wherein $R^2$ is benzyl, $R^3$ is methyl, $R^4$ is hydrogen, and $Y^1$ is a bond.

In certain embodiments of a compound of Formula (I), the compound is chosen from a compound of Formula (I-A-1), Formula (I-A-2), Formula (I-A-3), Formula (I-A-4), Formula (I-A-5), Formula (I-A-6), Formula (I-A-7), Formula (I-A-8), Formula (I-A-9), Formula (I-A-10), Formula (I-A-11), Formula (I-A-12), Formula (I-A-13), Formula (I-A-14), Formula (I-A-15), Formula (I-A-16), Formula (I-A-17), and Formula (I-A-18), or a pharmaceutically acceptable salt of any of the foregoing:

(I-A-1)

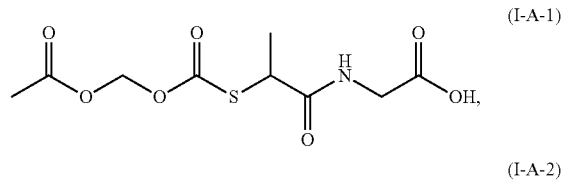

(I-A-2)

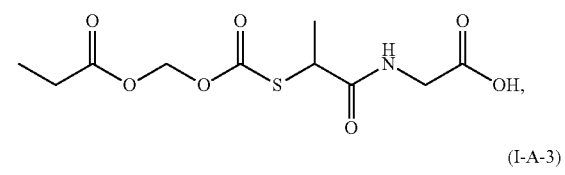

(I-A-3)

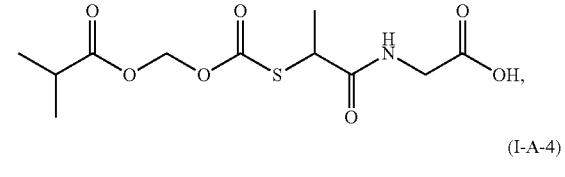

(I-A-4)

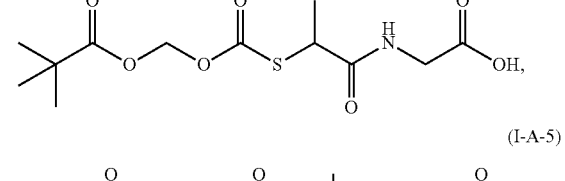

(I-A-5)

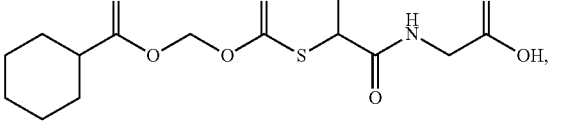

(I-A-6)

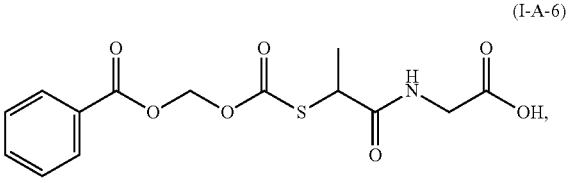

(I-A-7)

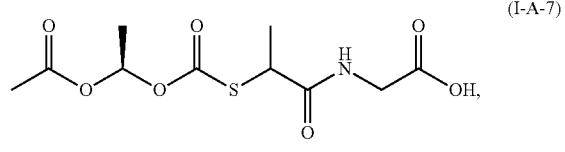

-continued (I-A-8)

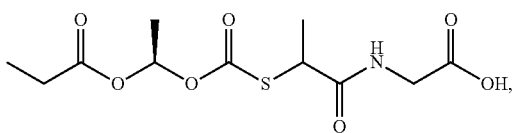

(I-A-9)

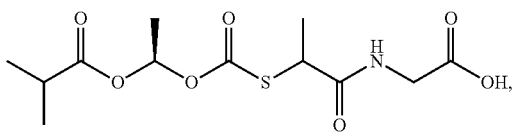

(I-A-10)

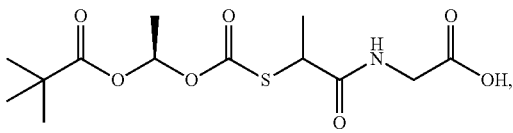

(I-A-11)

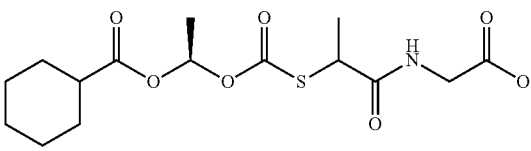

(I-A-12)

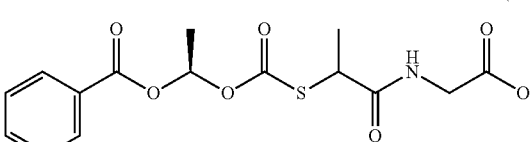

(I-A-13)

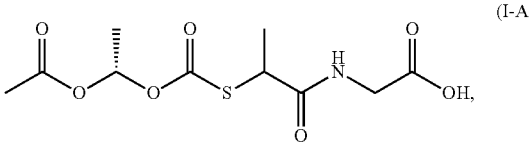

(I-A-14)

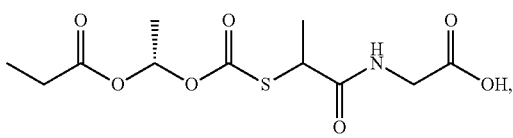

(I-A-15)

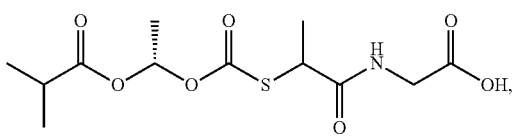

(I-A-16)

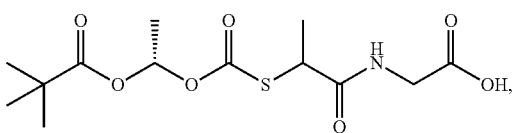

(I-A-17)

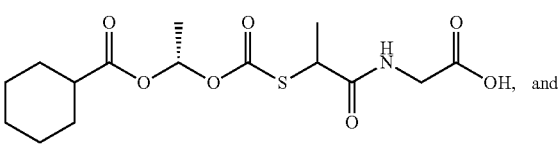

and

-continued (I-A-18)

[Chemical structure]

In certain embodiments of a compound of Formula (I), $R^1$ is methyl; and $W^1$ is the substituent of Formula (I-a), wherein $R^2$ is methyl, $R^3$ and $R^4$ are hydrogen, and $Y^1$ is a bond.

In certain embodiments of a compound of Formula (I), $R^1$ is ethyl; and $W^1$ is the substituent of Formula (I-a), wherein $R^2$ is methyl, $R^3$ and $R^4$ are hydrogen, and $Y^1$ is a bond.

In certain embodiments of a compound of Formula (I), $R^1$ is isopropyl; and $W^1$ is the substituent of Formula (I-a), wherein $R^2$ is methyl, $R^3$ and $R^4$ are hydrogen, and $Y^1$ is a bond.

In certain embodiments of a compound of Formula (I), $R^1$ is tert-butyl; and $W^1$ is the substituent of Formula (I-a), wherein $R^2$ is methyl, $R^3$ and $R^4$ are hydrogen, and $Y^1$ is a bond.

In certain embodiments of a compound of Formula (I), $R^1$ is phenyl; and $W^1$ is the substituent of Formula (I-a), wherein $R^2$ is methyl, $R^3$ and $R^4$ are hydrogen, and $Y^1$ is a bond.

In certain embodiments of a compound of Formula (I), $R^1$ is benzyl; and $W^1$ is the substituent of Formula (I-a), wherein $R^2$ is methyl, $R^3$ and $R^4$ are hydrogen, and $Y^1$ is a bond.

In certain embodiments of a compound of Formula (I), $R^1$ is 2-morpholinoethyl; and $W^1$ is the substituent of Formula (I-a), wherein $R^2$ is methyl, $R^3$ and $R^4$ are hydrogen, and $Y^1$ is a bond.

In certain embodiments of a compound of Formula (I), $R^1$ is 4-morpholinobutyl; and $W^1$ is the substituent of Formula (I-a), wherein $R^2$ is methyl, $R^3$ and $R^4$ are hydrogen, and $Y^1$ is a bond.

In certain embodiments of a compound of Formula (I), $R^1$ is methyl; and $W^1$ is the substituent of Formula (I-a), wherein $R^2$ is isopropyl, $R^3$ and $R^4$ are hydrogen, and $Y^1$ is a bond.

In certain embodiments of a compound of Formula (I), $R^1$ is ethyl; and $W^1$ is the substituent of Formula (I-a), wherein $R^2$ is isopropyl, $R^3$ and $R^4$ are hydrogen, and $Y^1$ is a bond.

In certain embodiments of a compound of Formula (I), $R^1$ is isopropyl; and $W^1$ is the substituent of Formula (I-a), wherein $R^2$ is isopropyl, $R^3$ and $R^4$ are hydrogen, and $Y^1$ is a bond.

In certain embodiments of a compound of Formula (I), $R^1$ is tert-butyl; and $W^1$ is the substituent of Formula (I-a), wherein $R^2$ is isopropyl, $R^3$ and $R^4$ are hydrogen, and $Y^1$ is a bond.

In certain embodiments of a compound of Formula (I), $R^1$ is phenyl; and $W^1$ is the substituent of Formula (I-a), wherein $R^2$ is isopropyl, $R^3$ and $R^4$ are hydrogen, and $Y^1$ is a bond.

In certain embodiments of a compound of Formula (I), $R^1$ is benzyl; and $W^1$ is the substituent of Formula (I-a), wherein $R^2$ is isopropyl, $R^3$ and $R^4$ are hydrogen, and $Y^1$ is a bond.

In certain embodiments of a compound of Formula (I), $R^1$ is 2-morpholinoethyl; and $W^1$ is the substituent of Formula (I-a), wherein $R^2$ is isopropyl, $R^3$ and $R^4$ are hydrogen, and $Y^1$ is a bond.

In certain embodiments of a compound of Formula (I), $R^1$ is 4-morpholinobutyl; and $W^1$ is the substituent of Formula (I-a), wherein $R^2$ is isopropyl, $R^3$ and $R^4$ are hydrogen, and $Y^1$ is a bond.

In certain embodiments of a compound of Formula (I), $R^1$ is methyl; and $W^1$ is the substituent of Formula (I-a), wherein $R^2$ is phenyl, $R^3$ and $R^4$ are hydrogen, and $Y^1$ is a bond.

In certain embodiments of a compound of Formula (I), $R^1$ is ethyl; and $W^1$ is the substituent of Formula (I-a), wherein $R^2$ is phenyl, $R^3$ and $R^4$ are hydrogen, and $Y^1$ is a bond.

In certain embodiments of a compound of Formula (I), $R^1$ is isopropyl; and $W^1$ is the substituent of Formula (I-a), wherein $R^2$ is phenyl, $R^3$ and $R^4$ are hydrogen, and $Y^1$ is a bond.

In certain embodiments of a compound of Formula (I), $R^1$ is tert-butyl; and $W^1$ is the substituent of Formula (I-a), wherein $R^2$ is phenyl, $R^3$ and $R^4$ are hydrogen, and $Y^1$ is a bond.

In certain embodiments of a compound of Formula (I), $R^1$ is phenyl; and $W^1$ is the substituent of Formula (I-a), wherein $R^2$ is phenyl, $R^3$ and $R^4$ are hydrogen, and $Y^1$ is a bond.

In certain embodiments of a compound of Formula (I), $R^1$ is benzyl; and $W^1$ is the substituent of Formula (I-a), wherein $R^2$ is phenyl, $R^3$ and $R^4$ are hydrogen, and $Y^1$ is a bond.

In certain embodiments of a compound of Formula (I), $R^1$ is 2-morpholinoethyl; and $W^1$ is the substituent of Formula (I-a), wherein $R^2$ is phenyl, $R^3$ and $R^4$ are hydrogen, and $Y^1$ is a bond.

In certain embodiments of a compound of Formula (I), $R^1$ is 4-morpholinobutyl; and $W^1$ is the substituent of Formula (I-a), wherein $R^2$ is phenyl, $R^3$ and $R^4$ are hydrogen, and $Y^1$ is a bond.

In certain embodiments of a compound of Formula (I), the compound is chosen from a compound of Formula (I-B-1), Formula (I-B-2), Formula (I-B-3), Formula (I-B-4), Formula (I-B-5), Formula (I-B-6), Formula (I-B-7), Formula (I-B-8), Formula (I-B-9), Formula (I-B-10), Formula (I-B-11), Formula (I-B-12), Formula (I-B-13), Formula (I-B-14), Formula (I-B-15), Formula (I-B-16), Formula (I-B-17), Formula (I-B-18), Formula (I-B-19), Formula (I-B-20), Formula (I-B-21), Formula (I-B-22), Formula (I-B-23), and Formula (I-B-24), or a pharmaceutically acceptable salt of any of the foregoing:

(I-B-1)

[Chemical structure]

(I-B-2)

[Chemical structure]

-continued
(I-B-3)
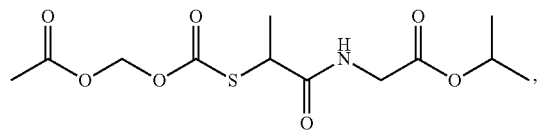
(I-B-4)
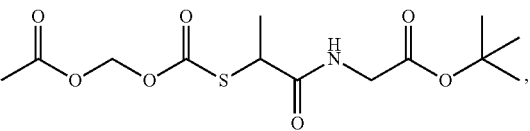
(I-B-5)
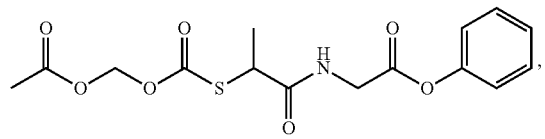
(I-B-6)
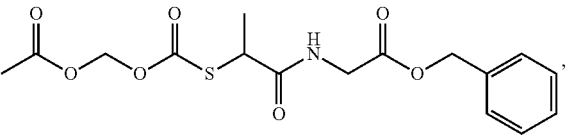
(I-B-7)
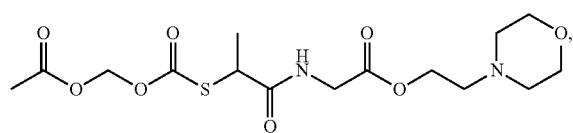
(I-B-8)
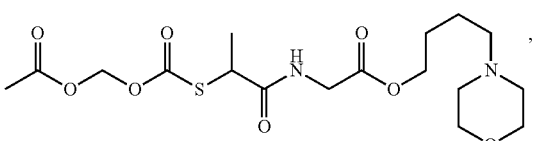
(I-B-9)
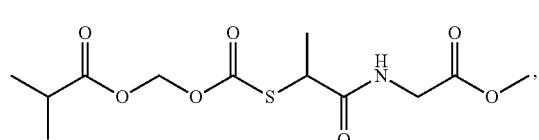
(I-B-10)
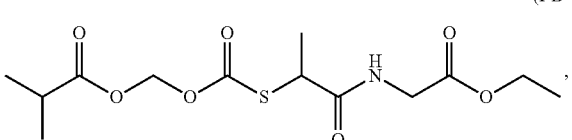
(I-B-11)
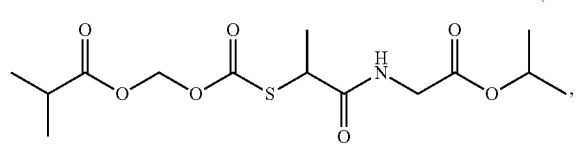
(I-B-12)
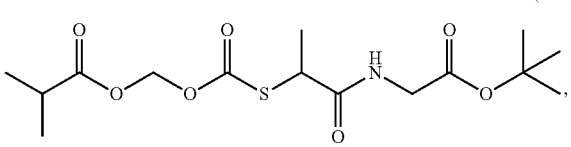
(I-B-13)
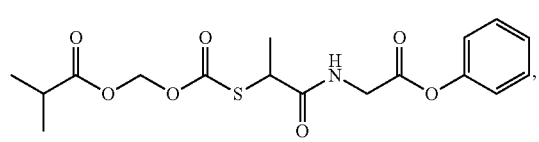
(I-B-14)
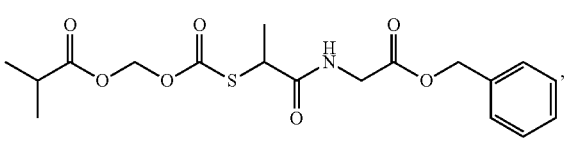
(I-B-15)
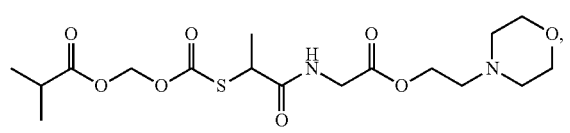
(I-B-16)
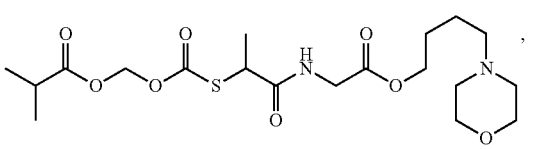
(I-B-17)
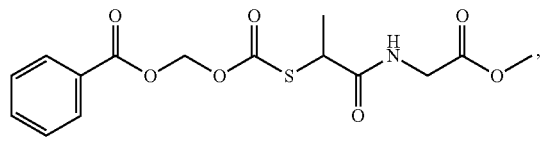
(I-B-18)
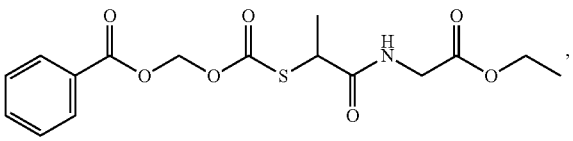
(I-B-19)
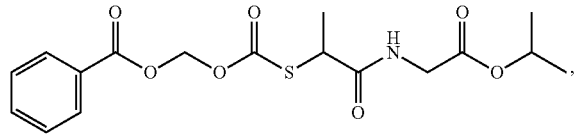
(I-B-20)
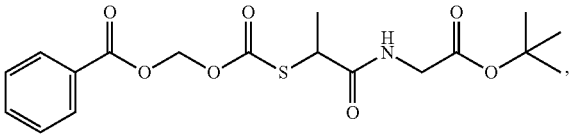

-continued

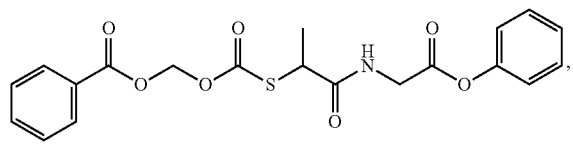
(I-B-21)

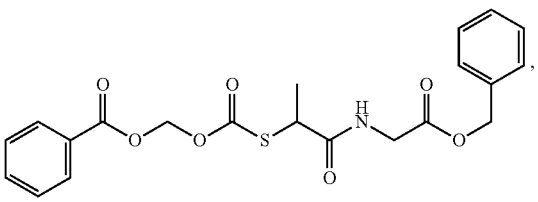
(I-B-22)

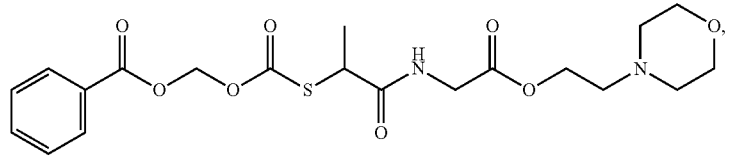
(I-B-23)

and

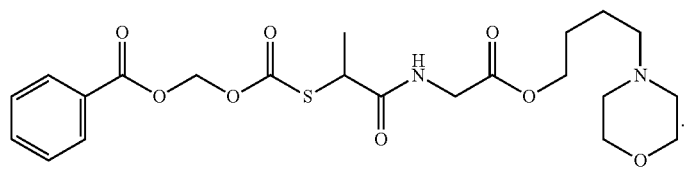
(I-B-24)

In certain embodiments of a compound of Formula (I), $R^1$ is hydrogen; and $W^1$ is the substituent of Formula (I-b), wherein $R^5$ is methyl.

In certain embodiments of a compound of Formula (I), $R^1$ is hydrogen; and $W^1$ is the substituent of Formula (I-b), wherein $R^5$ is phenyl.

In certain embodiments of a compound of Formula (I), $R^1$ is methyl; and $W^1$ is the substituent of Formula (I-b), wherein $R^5$ is methyl.

In certain embodiments of a compound of Formula (I), $R^1$ is ethyl; and $W^1$ is the substituent of Formula (I-b), wherein $R^5$ is methyl.

In certain embodiments of a compound of Formula (I), $R^1$ is isopropyl; and $W^1$ is the substituent of Formula (I-b), wherein $R^5$ is methyl.

In certain embodiments of a compound of Formula (I), $R^1$ is tert-butyl; and $W^1$ is the substituent of Formula (I-b), wherein $R^5$ is methyl.

In certain embodiments of a compound of Formula (I), $R^1$ is phenyl; and $W^1$ is the substituent of Formula (I-b), wherein $R^5$ is methyl.

In certain embodiments of a compound of Formula (I), $R^1$ is benzyl; and $W^1$ is the substituent of Formula (I-b), wherein $R^5$ is methyl.

In certain embodiments of a compound of Formula (I), $R^1$ is 2-morpholinoethyl; and $W^1$ is the substituent of Formula (I-b), wherein $R^5$ is methyl.

In certain embodiments of a compound of Formula (I), $R^1$ is 4-morpholinobutyl; and $W^1$ is the substituent of Formula (I-b), wherein $R^5$ is methyl.

In certain embodiments of a compound of Formula (I), the compound is chosen from a compound of Formula (I-C-1), Formula (I-C-2), Formula (I-C-3), Formula (I-C-4), Formula (I-C-5), Formula (I-C-6), Formula (I-C-7), Formula (I-C-8), Formula (I-C-9), and Formula (I-C-10), or a pharmaceutically acceptable salt of any of the foregoing:

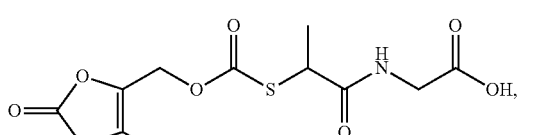
(I-C-1)

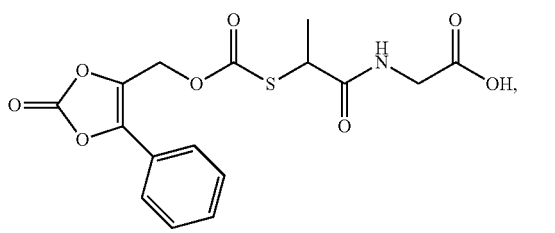
(I-C-2)

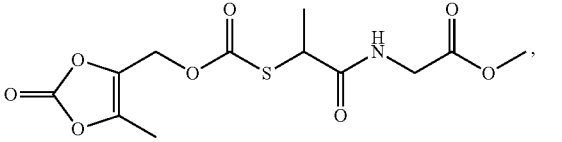
(I-C-3)

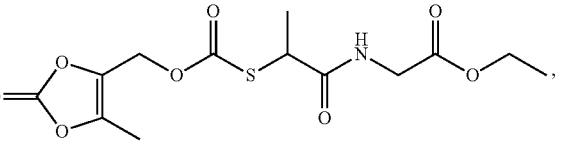
(I-C-4)

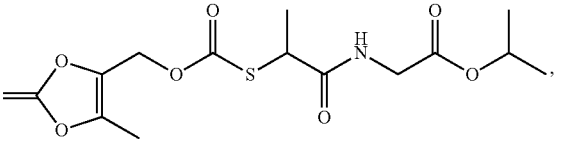
(I-C-5)

Synthesis

Compounds disclosed herein may be obtained via the synthetic methods illustrated in Schemes I-A to I-E. General synthetic methods useful in the synthesis of compounds described herein are available in the art. Starting materials useful for preparing compounds and intermediates thereof and/or practicing methods described herein are commercially available or can be prepared by well-known synthetic methods. The methods presented in the schemes provided by the present disclosure are illustrative rather than comprehensive. It will be apparent to those skilled in the art that many modifications, both to materials and methods, may be practiced without departing from the scope of the disclosure.

Compounds of Formula (I) can be prepared according to Schemes I-A to I-E:

Scheme I-E

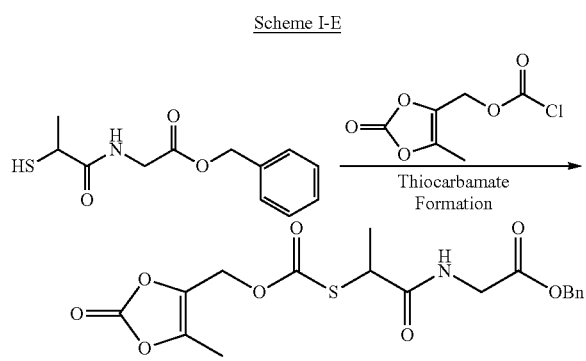

Pharmaceutical Compositions

Pharmaceutical compositions provided by the present disclosure may comprise a therapeutically effective amount of a compound of Formula (I) together with a suitable amount of one or more pharmaceutically acceptable vehicles so as to provide a composition for proper administration to a patient. Suitable pharmaceutical vehicles are described in the art.

In certain embodiments, a compound of Formula (I) may be incorporated into pharmaceutical compositions to be administered orally. Oral administration of such pharmaceutical compositions may result in uptake of a compound of Formula (I) throughout the intestine and entry into the systemic circulation. Such oral compositions may be prepared in a manner known in the pharmaceutical art and comprise a compound of Formula (I) and at least one pharmaceutically acceptable vehicle. Oral pharmaceutical compositions may include a therapeutically effective amount of a compound of Formula (I) and a suitable amount of a pharmaceutically acceptable vehicle, so as to provide an appropriate form for administration to a patient.

Compounds of Formula (I) may be incorporated into pharmaceutical compositions to be administered by any other appropriate route of administration including intradermal, intramuscular, intraperitoneal, intravenous, subcutaneous, intranasal, epidural, oral, sublingual, intracerebral, intravaginal, transdermal, rectal, inhalation, or topical.

Pharmaceutical compositions comprising a compound of Formula (I) and may be manufactured by means of conventional mixing, dissolving, granulating, dragee-making, levigating, emulsifying, encapsulating, entrapping, or lyophilizing processes. Pharmaceutical compositions may be formulated in a conventional manner using one or more physiologically acceptable carriers, diluents, excipients, or auxiliaries, which facilitate processing of compounds of Formula (I) or crystalline forms thereof and one or more pharmaceutically acceptable vehicles into formulations that can be used pharmaceutically. Proper formulation is dependent upon the route of administration chosen. Pharmaceutical compositions provided by the present disclosure may take the form of solutions, suspensions, emulsion, tablets, pills, pellets, capsules, capsules containing liquids, powders, sustained-release formulations, suppositories, emulsions, aerosols, sprays, suspensions, or any other form suitable for administration to a patient.

Pharmaceutical compositions provided by the present disclosure may be formulated in a unit dosage form. A unit dosage form refers to a physically discrete unit suitable as a unitary dose for patients undergoing treatment, with each unit containing a predetermined quantity of a compound of Formula (I) calculated to produce an intended therapeutic effect. A unit dosage form may be for a single daily dose, for administration 2 times per day, or one of multiple daily doses, e.g., 3 or more times per day. When multiple daily doses are used, a unit dosage form may be the same or different for each dose. One or more dosage forms may comprise a dose, which may be administered to a patient at a single point in time or during a time interval.

Pharmaceutical compositions comprising a compound of Formula (I) may be formulated for immediate release.

In certain embodiments, an oral dosage form provided by the present disclosure may be a controlled release dosage form. Controlled delivery technologies can improve the absorption of a drug in a particular region or regions of the gastrointestinal tract. Controlled drug delivery systems may be designed to deliver a drug in such a way that the drug level is maintained within a therapeutically effective window and effective and safe blood levels are maintained for a period as long as the system continues to deliver the drug with a particular release profile in the gastrointestinal tract. Controlled drug delivery may produce substantially constant blood levels of a drug over a period of time as compared to fluctuations observed with immediate release dosage forms. For some drugs, maintaining a constant blood and tissue concentration throughout the course of therapy is the most desirable mode of treatment. Immediate release of drugs may cause blood levels to peak above the level required to elicit a desired response, which may waste the drug and may cause or exacerbate toxic side effects. Controlled drug delivery can result in optimum therapy, and not only can reduce the frequency of dosing, but may also reduce the severity of side effects. Examples of controlled release dosage forms include dissolution controlled systems, diffusion controlled systems, ion exchange resins, osmotically controlled systems, erodable matrix systems, pH independent formulations, gastric retention systems, and the like.

An appropriate oral dosage form for a particular pharmaceutical composition provided by the present disclosure may depend, at least in part, on the gastrointestinal absorption properties of a compound of Formula (I) the stability of a compound of Formula (I) in the gastrointestinal tract, the pharmacokinetics of a compound of Formula (I) and the intended therapeutic profile. An appropriate controlled release oral dosage form may be selected for a particular compound of Formula (I). For example, gastric retention oral dosage forms may be appropriate for compounds absorbed primarily from the upper gastrointestinal tract, and sustained release oral dosage forms may be appropriate for compounds absorbed primarily from the lower gastrointestinal tract. Certain compounds are absorbed primarily from the small intestine. In general, compounds traverse the length of the small intestine in about 3 to 5 hours. For compounds that are not easily absorbed by the small intestine or that do not dissolve readily, the window for active agent absorption in the small intestine may be too short to provide a desired therapeutic effect.

In certain embodiments, pharmaceutical compositions provided by the present disclosure may be practiced with dosage forms adapted to provide sustained release of a compound of Formula (I) upon oral administration. Sustained release oral dosage forms may be used to release drugs over a prolonged time period and are useful when it is desired that a drug or drug form be delivered to the lower gastrointestinal tract. Sustained release oral dosage forms include any oral dosage form that maintains therapeutic concentrations of a drug in a biological fluid such as the plasma, blood, cerebrospinal fluid, or in a tissue or organ for a prolonged time period. Sustained release oral dosage forms include diffusion-controlled systems such as reservoir devices and matrix devices, dissolution-controlled systems, osmotic systems, and erosion-controlled systems. Sustained release oral dosage forms and methods of preparing the same are well known in the art.

An appropriate dose of a compound of Formula (I) or pharmaceutical composition comprising a compound of Formula (I) may be determined according to any one of several well-established protocols. For example, animal studies such as studies using mice, rats, dogs, and/or monkeys may be used to determine an appropriate dose of a pharmaceutical compound. Results from animal studies may be extrapolated to determine doses for use in other species, such as for example, humans.

Uses

Compounds of Formula (I) and pharmaceutical compositions thereof may be administered to a patient suffering from any disease including a disorder, condition, or symptom for which tiopronin is known or hereafter discovered to be therapeutically effective. Indication for which tiopronin has been prescribed, and hence for which a compound of Formula (I), or pharmaceutical compositions thereof are also expected to be effective, includes cystinuria. Other indications for which compounds of Formula (I) may be therapeutically effective include Wilson's disease, rheumatoid arthritis, chronic bronchopulmonary disease, austism, Gaucher's disease, cystic fibrosis, Parkinson's disease, multiple sclerosis, inflammatory bowel disease, and asthma.

Methods of treating a disease in a patient provided by the present disclosure comprise administering to a patient in need of such treatment a therapeutically effective amount of a compound of Formula (I). Compounds of Formula (I) or pharmaceutical compositions thereof may provide therapeutic or prophylactic plasma and/or blood concentrations of tiopronin following administration to a patient.

Compounds of Formula (I) may be included in a pharmaceutical composition and/or dosage form adapted for oral administration, although compound of Formula (I) may also be administered by any other appropriate route, such as for example, by injection, infusion, inhalation, transdermal, or absorption through epithelial or mucosal membranes (e.g., oral, rectal, and/or intestinal mucosa).

Compounds of Formula (I) may be administered in an amount and using a dosing schedule as appropriate for treatment of a particular disease. Daily doses of a compound of Formula (I) may range from about 0.01 mg/kg to about 500 mg/kg, from about 0.1 mg/kg to about 200 mg/kg, from about 1 mg/kg to about 50 mg/kg, and in certain embodiments, from about 5 mg/kg to about 25 mg/kg. In certain embodiments, compounds of Formula (I) may be administered at a dose over time from about 1 mg to about 20 g per day, from about 10 mg to about 10 g per day, and in certain embodiments from about 20 mg to about 5 g per day. An appropriate dose of a compound of Formula (I) may be determined based on several factors, including, for example, the body weight and/or condition of the patient being treated, the severity of the disease being treated, the incidence and/or severity of side effects, the manner of administration, and the judgment of the prescribing physician. Appropriate dose ranges may be determined by methods known to those skilled in the art.

Compounds of Formula (I) may be assayed in vitro and in vivo for the desired therapeutic or prophylactic activity prior to use in humans. In vivo assays, for example using appropriate animal models, may also be used to determine whether administration of a compound of Formula (I) is therapeutically effective.

In certain embodiments, a therapeutically effective dose of a compound of Formula (I) may provide therapeutic benefit without causing substantial toxicity including adverse side effects. Toxicity of compounds of Formula (I) and/or metabolites thereof may be determined using standard pharmaceutical procedures and may be ascertained by those skilled in the art. The dose ratio between toxic and therapeutic effect is the therapeutic index. A dose of a compound of Formula (I) may be within a range capable of establishing and maintaining a therapeutically effective circulating plasma and/or blood concentration of a compound of Formula (I) that exhibits little or no toxicity Tiopronin prodrug of Formula (I) may be used to treat diseases, disorders, conditions, and symptoms of any of the foregoing for which tiopronin is known to provide or is later found to provide therapeutic benefit. Tiopronin is known to be effective in treating cystinuria. Hence, compounds of Formula (I) may be used to treat the foregoing disease and disorder. The underlying etiology of any of the foregoing diseases being treated may have a multiplicity of origins. Further, in certain embodiments, a therapeutically effective amount of one or more compounds of Formula (I) may be administered to a patient, such as a human, as a preventative measure against various diseases or disorders.

Chronic Obstructive Pulmonary Disease

Chronic obstructive pulmonary disease (COPD), also known as chronic obstructive airway disease, is a group of diseases characterized by the pathological limitation of airflow in the airway that is not fully reversible, and includes conditions such as chronic bronchitis, emphysema, as well as other lung disorders such as asbestosis, pneumoconiosis, and pulmonary neoplasms (see, e.g., Barnes, Pharmacological Reviews 2004, 56(4), 515-548). The airflow limitation is usually progressive and associated with an abnormal inflammatory response of the lungs to noxious particles and gases. COPD is characterized by a shortness of breath the last for months or years, possibly accompanied by wheezing, and a persistent cough with sputum production. COPD is most often caused by tobacco smoking, although it can also be caused by other airborne irritants such as coal dust, asbestos, urban pollution, or solvents. COPD encompasses chronic obstructive bronchiolitis with fibrosis and obstruction of small airways, and emphysema with enlargement of airspaces and destruction of lung parenchyma, loss of lung elasticity, and closure of small airways.

The efficacy of administering at least one compound of Formula (I) for treating chronic obstructive pulmonary disease may be assessed using animal models of chronic obstructive pulmonary disease and in clinical studies.

Wilson's Disease

Wilson's disease is a genetic disease in which copper accumulates in liver and brain. The disorder is characterized by tiredness, increased bleeding tendency or confusion (due to hepatic encephalopathy), portal hypertension, mild cognitive deterioration, bradykinesia, dystonia, seizures and migraine.

The efficacy of tiopronin prodrugs of Formula (I) for treating Wilson's disease can be determined using animal models and in clinical trials.

Rheumatoid Arthritis

Rheumatoid arthritis is a chronic inflammatory disorder that typically affects the lining of small joints in hands and feet, causing painful swelling that can eventually result in bone erosion and joint deformity.

Efficacy of tiopronin prodrugs of Formula (I) for treating rheumatoid arthritis can be determined using animal models and in clinical trials.

Autism Spectrum Disorder

Autism spectrum disorder is characterized by social deficits and communication difficulties, stereotyped or repetitive behaviors and interests, sensory issues, and in some cases, cognitive delays.

Efficacy of tiopronin prodrugs of Formula (I) for treating autism spectrum disorder can be determined using animal models and in clinical trials.

Gaucher's Disease

Gaucher's disease is a genetic disease in which fatty substances (sphingolipids) accumulate in cells and certain organs. The disorder is characterized by bruising, fatigue, anemia, low blood platelets, and enlargement of the liver and spleen.

Efficacy of tiopronin prodrugs of Formula (I) for treating Gaucher's disease can be determined using animal models and in clinical trials.

Cystic Fibrosis

Cystic fibrosis is a life-threatening genetic disorder that causes severe damage to the lungs and digestive system. High dose oral N-acetylcysteine is thought to modulate inflammation in cystic fibrosis (Tirouvanziam et al., Proc. Natl. Acad. Sci. 2006, 103 (12), 4628-33).

The efficacy of tiopronin prodrugs of Formula (I) for cystic fibrosis may be assessed using animal and human models of cytic fibrosis and in clinical studies.

Parkinson's Disease

Parkinson's disease is a slowly progressive degenerative disorder of the nervous system characterized by tremor when muscles are at rest (resting tremor), slowness of voluntary movements, and increased muscle tone (rigidity). In Parkinson's disease, nerve cells in the basal ganglia, e.g., substantia nigra, degenerate, and thereby reduce the production of dopamine and the number of connections between nerve cells in the basal ganglia. As a result, the basal ganglia are unable to smooth muscle movements and coordinate changes in posture as normal, leading to tremor, incoordination, and slowed, reduced movement (bradykinesia) (Blandini, et al., Mol. Neurobiol. 1996, 12, 73-94).

The efficacy of tiopronin prodrugs of Formula (I) for treating Parkinson's disease may be assessed using animal and human models of Parkinson's disease and in clinical studies.

Multiple Sclerosis

Multiple sclerosis (MS) is an inflammatory autoimmune disease of the central nervous system caused by an autoimmune attack against the isolating axonal myelin sheets of the central nervous system. Demyelination leads to the breakdown of conduction and to severe disease with destruction of local axons and irreversible neuronal cell death. The symptoms of MS are highly varied with each individual patient exhibiting a particular pattern of motor, sensible, and sensory disturbances. MS is typified pathologically by multiple inflammatory foci, plaques of demyelination, gliosis, and axonal pathology within the brain and spinal cord, all of which contribute to the clinical manifestations of neurological disability (see e.g., Wingerchuk, Lab Invest 2001, 81, 263-281; and Virley, NeuroRx 2005, 2(4), 638-649). Although the causal events that precipitate MS are not fully understood, evidence implicates an autoimmune etiology together with environmental factors, as well as specific genetic predispositions. Functional impairment, disability, and handicap are expressed as paralysis, sensory and octintive disturbances spasticity, tremor, a lack of coordination, and visual impairment, which impact on the quality of life of the individual. The clinical course of MS can vary from individual to individual, but invariably the disease can be categorized in three forms: relapsing-remitting, secondary progressive, and primary progressive.

Assessment of MS treatment efficacy using tiopronin prodrugs of Formula (I) in clinical trials can be accomplished using tools such as the Expanded Disability Status Scale and the MS Functional as well as magnetic resonance imaging lesion load, biomarkers, and self-reported quality of life. Animal models of MS shown to be useful to identify and validate potential therapeutics include experimental autoimmune/allergic encephalomyelitis (EAE) rodent models that simulate the clinical and pathological manifestations of MS and nonhuman primate EAE models.

Inflammatory Bowel Disease (Crohn's Disease, Ulcerative Colitis)

Inflammatory bowel disease (IBD) is a group of inflammatory conditions of the large intestine and in some cases, the small intestine that includes Crohn's disease and ulcerative colitis. Crohn's disease, which is characterized by areas of inflammation with areas of normal lining in between, can affect any part of the gastrointestinal tract from the mouth to the anus. The main gastrointestinal symptoms are abdominal pain, diarrhea, constipation, vomiting, weight loss, and/or weight gain. Crohn's disease can also cause skin rashes, arthritis, and inflammation of the eye. Ulcerative colitis is characterized by ulcers or open sores in the large intestine or colon. The main symptom of ulcerative colitis is typically constant diarrhea with mixed blood of gradual onset. Other types of intestinal bowel disease include collagenous colitis, lymphocytic colitis, ischaemic colitis, diversion colitis, Behcet's colitis, and indeterminate colitis.

The efficacy of tiopronin prodrugs for treating inflammatory bowel disease can be evaluated using animal models and in clinical trials. Useful animal models of inflammatory bowel disease are known.

Asthma

Asthma is reversible airway obstruction in which the airway occasionally constricts, becomes inflamed, and is lined with an excessive amount of mucus. Symptoms of asthma include dyspnea, wheezing, chest tightness, and cough. Asthma episodes may be induced by airborne allergens, food allergies, medications, inhaled irritants, physical exercise, respiratory infection, psychological stress, hormonal changes, cold weather, or other factors.

The efficacy of tiopronin prodrugs of Formula (I) for treating asthma can be assessed using animal models and in clinical trials.

Interstitial Lung Disease

Interstitial lung disease (ILD), also known as diffuse parenchymal lung disease (DPLD), refers to a group of lung diseases affecting the interstitium. The term idiopathic pulmonary fibrosis is used to describe interstitial lung disease for which no obvious cause can be identified.

The efficacy of tiopronin prodrugs of Formula (I) for treating interstitial lung disease can be assessed using animal models and in clinical trials.

Administration

Compounds of Formula (I) and pharmaceutical compositions thereof may be administered orally or by any other appropriate route, for example, by infusion or bolus injection, by absorption through epithelial or mucocutaneous linings (e.g., oral mucosa, rectal, and intestinal mucosa, etc.). Other suitable routes of administration include, but are not limited to, intradermal, intramuscular, intraperitoneal, intravenous, subcutaneous, intranasal, epidural, oral, sublingual, intracerebral, intravaginal, transdermal, rectal, inhalation, or topical.

Administration may be systemic or local. Various delivery systems are known, e.g., encapsulation in liposomes, microparticles, microcapsules, capsules, etc.) that may be used to administer a compound and/or pharmaceutical composition.

The amount of a compound of Formula (I) that will be effective in the treatment of a disease in a patient will depend, in part, on the nature of the condition and can be determined by standard clinical techniques known in the art. In addition, in vitro or in vivo assays may be employed to help identify optimal dosage ranges. A therapeutically effective amount of a compound of Formula (I) to be administered may also depend on, among other factors, the subject being treated, the weight of the subject, the severity of the disease, the manner of administration, and the judgment of the prescribing physician.

For systemic administration, a therapeutically effective dose may be estimated initially from in vitro assays. For example, a dose may be formulated in animal models to achieve a beneficial circulating composition concentration range. Initial doses may also be estimated from in vivo data, e.g., animal models, using techniques that are known in the art. Such information may be used to more accurately determine useful doses in humans. One having ordinary skill in the art may optimize administration to humans based on animal data.

A dose may be administered in a single dosage form or in multiple dosage forms. When multiple dosage forms are used the amount of compound contained within each dosage form may be the same or different. The amount of a compound of Formula (I) contained in a dose may depend on the route of administration and whether the disease in a patient is effectively treated by acute, chronic, or a combination of acute and chronic administration.

In certain embodiments an administered dose is less than a toxic dose. Toxicity of the compositions described herein may be determined by standard pharmaceutical procedures in cell cultures or experimental animals, e.g., by determining the LD50 (the dose lethal to 50% of the population) or the LD100 (the dose lethal to 100% of the population). The dose ratio between toxic and therapeutic effect is the therapeutic index. In certain embodiments, a tiopronin prodrug may exhibit a high therapeutic index. The data obtained from these cell culture assays and animal studies may be used in formulating a dosage range that is not toxic for use in humans. A dose of a tiopronin prodrug provided by the present disclosure may be within a range of circulating concentrations in for example the blood, plasma, or central nervous system, that include the effective dose and that exhibits little or no toxicity. A dose may vary within this range depending upon the dosage form employed and the route of administration utilized. In certain embodiments, an escalating dose may be administered.

Combination Therapy

Methods provided by the present disclosure further comprise administering one or more pharmaceutically active compounds in addition to a compound of Formula (I). Such compounds may be provided to treat the same disease or a different disease than the disease being treated with the tiopronin prodrug of Formula (I).

In certain embodiments, a compound of Formula (I) may be used in combination with at least one other therapeutic agent. In certain embodiments, a compound of Formula (I) may be administered to a patient together with another compound for treating diseases and conditions involving immunological, autoimmune, and/or inflammatory processes including: psoriasis; asthma, chronic obstructive pulmonary diseases, and arthritis; cardiac insufficiency including left ventricular insufficiency, myocardial infarction and angina pectoris; mitochondrial and neurodegenerative diseases such as Parkinson's disease, Alzheimer's disease, Huntington's disease, retinopathia pigmentosa and mitochondrial encephalomyopathy; transplantation rejection; autoimmune diseases including multiple sclerosis (MS); ischemia and reperfusion injury (AGE-induced genome damage; and others. In certain embodiments, a compound of Formula (I) may be administered to a patient together with another compound for treating psoriasis, multiple sclerosis, an inflammatory bowel disease, asthma, chronic obstructive pulmonary disease, and arthritis.

A compound of Formula (I) and the at least one other therapeutic agent may act additively or, and in certain embodiments, synergistically. The at least one additional therapeutic agent may be included in the same dosage form as a compound of Formula (I) or may be provided in a separate dosage form. Methods provided by the present disclosure can further include, in addition to administering a compound of Formula (I), administering one or more therapeutic agents effective for treating the same or different disease than the disease being treated by a compound of Formula (I). Methods provided by the present disclosure include administration of a compound of Formula (I) and one or more other therapeutic agents provided that the combined administration does not inhibit the therapeutic efficacy of the tiopronin prodrug and/or does not typically produce significant and/or substantial adverse combination effects.

In certain embodiments, dosage forms comprising a compound of Formula (I) may be administered concurrently with the administration of another therapeutic agent, which may be part of the same dosage form as, or in a different dosage form than that comprising a compound of Formula (I). A compound of Formula (I) may be administered prior or subsequent to administration of another therapeutic agent. In certain embodiments of combination therapy, the combination therapy may comprise alternating between administering a compound of Formula (I) and a composition comprising another therapeutic agent, e.g., to minimize adverse drug effects associated with a particular drug. When a compound of Formula (I) is administered concurrently with another therapeutic agent that potentially may produce an adverse drug effect including, but not limited to, toxicity, the other therapeutic agent may advantageously be administered at a dose that falls below the threshold at which the adverse drug reaction is elicited.

In certain embodiments, dosage forms comprising a compound of Formula (I) may be administered with one or more substances to enhance, modulate and/or control release, bioavailability, therapeutic efficacy, therapeutic potency, stability, and the like of a tiopronin prodrug of Formula (I). For example, to enhance the therapeutic efficacy of a tiopronin prodrug of Formula (I), the tiopronin prodrug of Formula (I) may be co-administered with one or more active agents to increase the absorption or diffusion of a compound of Formula (I) from the gastrointestinal tract to the systemic circulation, or to inhibit degradation of the tiopronin prodrug of Formula (I) in the blood of a patient. In certain embodiments, a compound of Formula (I) may be co-administered with an active agent having pharmacological effects that enhance the therapeutic efficacy of a compound of Formula (I).

In certain embodiments, a compound of Formula (I) or a pharmaceutical composition thereof may be administered to a patient for treating psoriasis in combination with a therapy or another therapeutic agent known or believed to be effective in treating psoriasis. Drugs useful for treating psoriasis include steroids such as flurandrenolide, fluocinonide, alclometasone, amcinonide, desonide, halcinonide, triamcinolone, clobetasol, clocortolone, mometasone, desoximetasone, and halobetasol; anti-rheumatics such as etanercept, infiximab, and adalimumab; immunosuppressive agents such as cyclosporine, alefacept, and efalizumab; psoralens such as methoxsalen; and other such as calcipotriene, methotrexate, hydrocortisone/pramoxine, acitretin, betamethasone/calcipotriene, tazaraotene, benzocaine/pyrilamine/zinc oxide, and ustekinumab.

In certain embodiments, a compound of Formula (I) or a pharmaceutical composition thereof may be administered to a patient for treating inflammatory arthritis such as rheumatoid arthritis, juvenile rheumatoid arthritis, psoriatic arthritis, and ankylosing spondylitis in combination with a therapy or another therapeutic agent known or believed to be effective in treating inflammatory arthritis such as rheumatoid arthritis, juvenile rheumatoid arthritis, psoriatic arthritis, and ankylosing spondylitis.

Drugs useful for treating rheumatoid arthritis include non-steroidal anti-inflammatory agents such as ibuprofen, ketoprofen, salicylate, diclofenac, nabumetone, naproxen, meloxicam, sulindac, flurbiprofen, indomethacin, tolmetin, piroxicam, fenoprofen, oxaprozin, and etodolac; antiheumatics such as entanercept, adalimumab, infliximab, hydroxychloroquine, leflunomide, azathioprine, penicillamine, methotrexate, anakinra, auranofin, rituximab, aurothioglucose, tocilizumab, and golimumab; cox-2 inhibitors such as celecoxib and vadecoxib; corticosteroids such as triamcinolone; glucocorticoids such as methylprednisolone and prednisone; and others such as sulfasalazine.

Drugs useful for treating juvenile rheumatoid arthritis include adalimumab, abatacept, and infliximab.

Drugs useful for treating psoriatic arthritis include etanercept, adalimumab, triamcinolone, cortisone, infliximab, and golimumab.

Drugs useful for treating ankylosing spondylitis include adalimumab, celecoxib, diclofenac, etanercept, golimumab, indomethacin infliximab, naptoxen, olsalazine, salicylates, sulfindac, and triamcinolone.

In certain embodiments, a compound of Formula (I) or a pharmaceutical composition thereof may be administered to a patient for treating psoriatic arthritis in combination with a therapy or another therapeutic agent known or believed to be effective in treating psioriatic arthritis. Drugs useful for treating psioriatic arthritis include etanercept, adalimumab, triamcinolone, cortisone, infliximab, and golimumab.

In certain embodiments, a compound of Formula (I) or a pharmaceutical composition thereof may be administered to a patient for treating autoimmune diseases such as lupus in combination with a therapy or another therapeutic agent known or believed to be effective in treating autoimmune diseases such as lupus. Drugs useful for treating lupus include hydrochlooquine, triamcinolone, salicylate, azathioprine, and abetimus.

In certain embodiments, a compound of Formula (I) or a pharmaceutical composition thereof may be administered to a patient for treating multiple sclerosis in combination with a therapy or another therapeutic agent known or believed to be effective in treating multiple sclerosis. Drugs useful for treating multiple sclerosis include interferon β-1a, interferon β-1b, glatiramer, modafinil, azathioprine, predisolone, mycophenolate mofetil, mitoxantrone, and natalizumab. Other examples of drugs useful for treating MS include Examples of drugs useful for treating MS include corticosteroids such as methylprednisolone; IFN-β such as IFN-β1a and IFN-β1b; glatiramer acetate; monoclonal antibodies that bind to the very late antigen-4 (VLA-4) integrin such as natalizumab; immunomodulatory agents such as FTY 720 sphinogosie-1 phosphate modulator and COX-2 inhibitors such as BW755c, piroxicam, and phenidone; and neuroprotective treatments including inhibitors of glutamate excitotoxicity and iNOS, free-radical scavengers, and cationic channel blockers; memantine; AMPA antagonists such as topiramate; and glycine-site NMDA antagonists.

In certain embodiments, a compound of Formula (I) or a pharmaceutical composition thereof may be administered to a patient for treating inflammatory bowel disease in combination with a therapy or another therapeutic agent known or believed to be effective in treating inflammatory bowel disease. Drugs useful for treating inflammatory bowel disease include cromolyn and mercaptopurine; and more particularly for treating Crohn's disease include certolizumab, budesonide, azathioprine, sulfasalazine, metronidazole, adalimumab, mercaptopurine, infliximab, mesalamine, and natalizumab; and for treating ulcerative colitis include balsalazide, infliximab, azathioprine, mesalamine, and cyclosporine.

In certain embodiments, a compound of Formula (I) or a pharmaceutical composition thereof may be administered to a patient for treating cystic fibrosis in combination with a therapy or another therapeutic agent known or believed to be effective in treating cystic fibrosis. Drugs useful for treating cystic fibrosis include ivacaftor and lumacaftor.

In certain embodiments, tiopronin prodrugs provided by the present disclosure and pharmaceutical compositions thereof may be administered to a patient for treating asthma in combination with a therapy or another therapeutic agent known or believed to be effective in treating asthma, or in certain embodiments, a disease, disorder, or condition associated with asthma. Examples of drugs useful in treating asthma include albuterol, aminophylline, beclomethasone, bitolterol, budesonide, cromolyn, ephedrine, epinephrine, flunisolide, fluticasone, formoterol, hydrocortisone, isoproterenol, levalbuterol, methylprednisolone, prednisolone, prednisone, pirbuterol, metaproterenol, racepinephrine, omalizumab, oxytriphylline, mometusone, montelukast, nedocromil, oxtriphylline, pirbuterol, salmeterol, terbutaline, theophylline, triamcinolone, zafirlukast, and zileuton.

In certain embodiments, tiopronin prodrugs provided by the present disclosure and pharmaceutical compositions thereof may be administered to a patient for treating chronic obstructive pulmonary disease in combination with a therapy or another therapeutic agent known or believed to be effective in treating chronic obstructive pulmonary disease, or in certain embodiments, a disease, disorder, or condition associated with chronic obstructive pulmonary disease. Examples of drugs useful for treating chronic obstructive pulmonary disease include albuterol, arformoterol, azithromycin, bitolterol, epinephrine, fluticasone, formoterol, ipratropium, isoproterenol, levabuterol, metaproterenol, pirbuterol, racepinephrine, salmeterol, and tiotropium. Useful drugs for treating chronic obstructive pulmonary disease further include bronchodialators such as β2 agonists such as salbutamol, bambuterol, clenbuterol, fenoterol, and formoterol; M3 antimuscarinics such as ipratropium; leukotriene antagonists such as montelukast, pranlukast, and zafirlukast; cromones such as cromoglicate and nedocromil; xanthines such as theophylline; corticosteroids such as beclomethasone, mometasone, and fluticasone; and TNF antagonists such as infliximab, adalimumab, and etanercept. Other treatments for chronic obstructive pulmonary disease include oxygen therapy, and pulmonary rehabilitation.

In certain embodiments, prodrugs provided by the present disclosure and pharmaceutical compositions thereof may be administered to a patient for treating angiogenesis in combination with a therapy or another therapeutic agent known or believed to be effective in treating angiogenesis. Useful drugs for treating angiogenesis include angiostatin, endostatin, vitaxin, bevacizumab, thalidomide, batimastat, marimastat, carboxyamidotraizole, TNP-470, CM101, IFN-α, IL-12, platelet factor-4, suramin, SU5416, thrombospondin, VEGFR, angiostatic steroids, cartilage-derived angiogenesis inhibitory factor, matrix metalloproteinase inhibitors, 2-methoxyestradiol, tecogalan, thrombospondin, prolactin, αvβ3 inhibitors, and linomide.

In certain embodiments, prodrugs provided by the present disclosure and pharmaceutical compositions thereof may be administered to a patient for treating transplant rejection in combination with a therapy or another therapeutic agent known or believed to be effective in treating transplant rejection. Useful drugs for treating transplant rejection include calcineurin inhibitors such as cyclosporine and tacrolimus, mTOR inhibitors such as sirolimus and everolimus, anti-proliferatives such as azathioprine and mycophenolic acid; corticosteroids such as monoclonal anti-IL2Rα receptor antibodies including basiliximab and daclizumab; and polyclonal anti-T-cell antibodies including anti-thymocyte globulin and anti-lymphocyte globulin.

In certain embodiments, prodrugs provided by the present disclosure and pharmaceutical compositions thereof may be administered to a patient for treating transplantation rejection in combination with a therapy or another therapeutic agent known or believed to be effective in treating transplantation rejection. Examples of drugs useful in transplantation rejection include corticosteroids such as dexamethasone, prednisolone, and prednisone; globulins such as antilymphocyte globulin and antithymocyte globulin; macrolide immunosuppressants such as sirolimus, tacrolimus, and everolimus; mitotic inhibitors such as azathiprine, cylophosphamide, and methotrexate; monoclonal antibodies such as basiliximab, daclizumab, infliximab, muromonoab; fungal metabolites such as cyclosporine; and others such as glatiramer and mycophenolate.

In certain embodiments, prodrugs provided by the present disclosure and pharmaceutical compositions thereof may be administered to a patient for treating cardiac insufficiency in combination with a therapy or another therapeutic agent known or believed to be effective in treating cardiac insufficiency. Useful drugs for treating cardiac insufficiency include antitensin-modulating agents, diuretics such as furosemide, bumetanie, hydrochlorothiazide, chlorthalidone, chlorthiazide, spironolactone, eplerenone: beta blockers such as bisoprolol, carvedilol, and metroprolol; positive inotropes such as digoxin, milrinone, and dobutamine; alternative vasodilators such as isosorbide dinitrate/hydralazine; aldosterone receptor antagonists; recombinant neuroendocrine hormones such as nesiritide; and vasopressin receptor antagonists such as tolvaptan and conivaptan.

In certain embodiments, prodrugs provided by the present disclosure and pharmaceutical compositions thereof may be administered to a patient for treating a mitochondrial disease such as a neurodegenerative disorder in combination with a therapy or another therapeutic agent known or believed to be effective in treating a mitochondrial disease such as a neurodegenerative disorder. In certain embodiments, a neurodegenerative disorder is chosen from Alzheimer's disease, Parkinson's disease, Huntington's disease, and amyotrophic lateral sclerosis.

Therapeutic agents useful for treating Parkinson's disease include dopamine precursors such levodopa, dopamine agonists such as bromocriptine, pergolide, pramipexole, and ropinirole, MAO-B inhibitors such as selegiline, anticholinergic drugs such as benztropine, trihexyphenidyl, tricyclic antidepressants such as amitriptyline, amoxapine, clomipramine, desipramine, doxepin, imipramine, maprotiline, nortriptyline, protriptyline, amantadine, and trimipramine, some antihistamines such as diphenhydramine; antiviral drugs such as amantadine; and beta blockers such as propranolol.

Useful drugs for treating Alzheimer's disease include rosiglitazone, roloxifene, vitamin E, donepezil, tacrine, rivastigmine, galantamine, and memantine.

Useful drugs for treating symptoms of Huntington's disease include antipsychotics such as haloperidol, chiorpromazine and olanzapine to control hallucinations, delusions and violent outbursts; antidepressants such as fluoxetine, sertraline, and nortryiptyline to control depression and obsessive-compulsive behavior; tranquilizers such as benzodiazepines, paroxetine, venflaxin and beta-blockers to control anxiety and chorea; mood stabilizers such as lithium, valproate, and carbamzepine to control mania and bipolar disorder; and botulinum toxin to control dystonia and jaw clenching. Useful drugs for treating symptoms of Huntington's disease further include selective serotonin reuptake inhibitors (SSRI) such as fluoxetine, paroxetine, sertraline, escitalopram, citalopram, fluvosamine; norepinephrine and serotoiun reuptake inhibitors (NSRI) such as venlafaxine and duloxetine, benzodiazepines such as clonazepam, alprazolam, diazepam, and lorazepam, tricyclic antidepressants such as amitriptyline, nortnriptyline, and imipramine; and atypical antidepressants such as busipirone, bupriopion, and mirtazepine for treating the symptoms of anxiety and depression; atomoxetine, dextroamphetamine, and modafinil for treating apathy symptoms; amantadine, memantine, and tetrabenazine for treating chorea symptoms; citalopram, atomoxetine, memantine, rivastigmine, and donepezil for treating cognitive symptoms; lorazepam and trazedone for treating insomnia; valproate, carbamazepine and lamotrigine for treating symptoms of irritability; SSRI antidepressants such as fluoxetine, paroxetine, sertaline, and fluvoxamine, NSRI antidepressants such as venlafaxine, and others such as mirtazepine, clomipramine, lomotrigine, gabapentin, valproate, carbamazepine, olanzapine, rispiridone, and quetiapine for treating symptoms of obsessive-compulsive disorder; haloperidol, quetiapine, clozapine, risperidone, olanzapine, ziprasidone, and aripiprazole for treating psychosis; and pramipexole, levodopa and amantadine for treating rigidity.

Useful drugs for treating ALS include riluzole. Other drugs of potential use in treating ALS include memantine, tamoxifen, thalidomide, ceftriaxone, sodium phenyl butyrate, celecoxib, glatiramer acetate, busipirone, creatine, minocycline, coenzyme Q10, oxandrolone, IGF-1, topiramate, xaliproden, and indinavir. Drugs such as baclofen and diazepam can be useful in treating spasticity associated with ALS.

In certain embodiments, a compound of Formula (I) or a pharmaceutical composition thereof may be administered to a patient in combination with a therapy or another therapeutic agent known or believed to be effective in inhibiting TNF function.

Examples of drugs known to inhibit TNF function include infliximab, adalimumab, etanercept, certolizumab, golimumab, pentoxifylline, quanylhydrozone, thalidomide, flavonoids such as narigenin, resveratrol and quecetin, alkaloids such as lycorine, terpenes such as acanthoic acid, fatty acids such as 13-HOA, and retinoids such as retinoic acid.

EXAMPLES

The following examples describe in detail the synthesis of compounds of Formula (I). It will be apparent to those skilled in the art that many modifications, both to materials and methods, may be practiced without departing from the scope of the disclosure.

General Experimental Protocols

All reagents and solvents that can be purchased from commercial suppliers may be used without further purification or manipulation. Non-commercially available reagents may be synthesized from commercially available starting materials, and by adapting methods well known in the art.

Analytical LC/MS was performed on a Agilent 1100 equipped with AB Sciex API 2000 or a Waters 2790 equipped with a Waters Micromass QZ mass spectrometer and a Phenomenex Luna C-18 analytical column. Preparative HPLC purification was performed on a Agilent 1100. Both analytical and preparative HPLC used acetonitrile/water gradients containing 0.05% formic acid. Normal-phase silica gel purification was performed on a ISCO CombiFlash Companion purification system using either a mixture of methanol and dichloromethane or ethyl acetate and hexanes. Chemical names were generated with Accelrys Draw 4.1 SP1, version MDL.Draw.Editor 4.1. 100.70 (Accelrys, Inc., San Diego, Calif.).

General Synthetic Procedure

General Procedure: Thiocarbamate Formation

A thiol-containing compound (1.0 equivalent) is combined with an activated ester such as (2,5-dioxopyrrolidin-1-yl)oxycarbonyloxymethyl acetate (1.0 to 3.0 equivalents) in 1-20 mL/1.0 mmol of an inert solvent such as dichloromethane (DCM), ethyl acetate (EtOAc), N-methylpyrrolidone (NMP), N,N-dimethylformamide (DMF), N,N-dimethylacetamide (DMA, DMAc), acetonitrile (ACN, MeCN), dimethylsulfoxide (DMSO), tetrahydrofuran (THF), toluene, water, or mixtures thereof. To the solution, an appropriate inorganic base (1.0 to 5.0 equivalents) such as NaHCO$_3$, Na$_2$CO$_3$, KHCO$_3$, K$_2$CO$_3$, CsHCO$_3$, and Cs$_2$CO$_3$ or an organic secondary or tertiary base such as dicyclohexylamine (DCHA), triethylamine (TEA), and diisopropylethylamine (DIEA) is added. The reaction mixture is stirred from about 1 to about 72 h at a temperature between 0° C. to 40° C. The mixture is then diluted with an appropriate organic solvent such as methyl tert-butyl ether (MTBE), diethyl ether (Et$_2$O), ethylacetate (EtOAc), dichloromethane (DCM), or mixtures thereof, washed with water and brine, and dried over anhydrous sodium sulfate (Na$_2$SO$_4$) or magnesium sulfate (MgSO$_4$). After filtration, the organic solvents are removed under reduced pressure using a rotary evaporator. If required, the crude reaction products are further purified by well known purification techniques such as silica gel flash column chromatography, mass-guided reversed-phase preparative HPLC/lyophilization, precipitation, or crystallization.

General Procedure: Amide Formation

A primary or secondary amine-containing compound (1.0 to 2.0 equivalents) is combined with carboxylic acid-containing compound (0.8 to 1.2 equivalents) in 1-10 mL/1.0 mmol of an inert solvent such as dichloromethane (DCM), ethyl acetate (EtOAc), N-methylpyrrolidone (NMP), N,N-dimethylformamide (DMF), N,N-dimethylacetamide (DMA, DMAc), acetonitrile (MeCN), dimethylsulfoxide (DMSO), tetrahydrofuran (THF), toluene, or mixtures thereof. To the solution, an appropriate organic secondary or tertiary base (2.0 to 5.0 equivalents) such as dicyclohexylamine (DCHA), triethylamine (TEA), or diisopropylethylamine (DIEA), a catalyst (0.0 to 2.0 equivalents) such as N,N-dimethylpyridin-4-amine (DMAP), and a coupling agent (1.0 to 3.0 equivalents) such as N-(3-dimethylaminopropyl)-N'-ethylcarbodiimide hydrochloride (EDAC), N,N,N',N'-tetramethyl-O-(1H-benzotriazol-1-yl)uronium hexafluorophosphate (HBTU), 1-[bis(dimethylamino)methylene]-1H-1,2,3-triazolo[4,5-b]pyridinium 3-oxid hexafluorophosphate (HATU), benzotriazol-1-yl-oxytripyrrolidinophosphonium hexafluorophosphate (ByBOP), or N,N'-dicyclohexylcarbodiimide (DCC), are added. The reaction mixture is stirred from about 1 to about 24 h at a temperature between 0° C. to 40° C. The mixture is then diluted with an appropriate organic solvent such as methyl tert-butyl ether (MTBE), diethyl ether (Et$_2$O), ethylacetate (EtOAc), dichloromethane (DCM), or mixtures thereof, washed with water and brine, and dried over anhydrous magnesium sulfate (MgSO$_4$). After filtration, the organic solvents are removed under reduced pressure using a rotary evaporator. If required, the crude reaction products are further purified by well known purification techniques such as silica gel flash column chromatography, mass-guided reversed-phase preparative HPLC/lyophilization, precipitation, or crystallization.

Example 1

2-[2-(Acetoxymethoxycarbonylsulfanyl)propanoylamino]acetic acid (1)

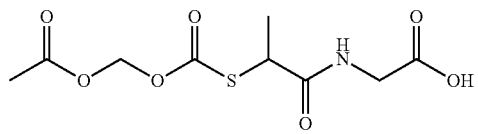 [SMILES: CC(=O)OCOC(=O)SC(C)C(=O)NCC(=O)O]

A mixture of tiopronin (0.10 g, 1.0 eq), (2,5-dioxopyrrolidin-1-yl)oxycarbonyloxymethyl acetate (1.0 eq), and NaHCO$_3$ (or TEA) (2.0 eq) in ACN/water (or DMF) (5 mL) was stirred at 20° C. overnight. The reaction was concentrated in vacuo to a residue and then purified by reverse-phase (C-18) liquid chromatography using water and acetonitrile as eluents to yield compound (1). MS (ESI): m/z 280.0 (M+H)+.

Example 2

2-[2-(2-Methylpropanoyloxymethoxycarbonylsulfanyl)propanoylamino]acetic acid (2)

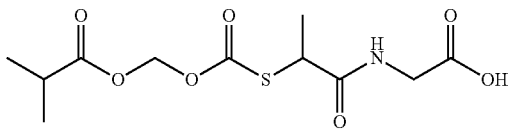 [SMILES: CC(C)C(=O)OCOC(=O)SC(C)C(=O)NCC(=O)O]

Compound (2) was prepared according to the method described in Example 1 and substituting (2,5-dioxopyrrolidin-1-yl)oxycarbonyloxymethyl acetate with (2,5-dioxopyrrolidin-1-yl)oxycarbonyloxymethyl 2-methylpropanoate. MS (ESI): m/z 308.1 (M+H)+.

Example 3

2-[2-(2,2-Dimethylpropanoyloxymethoxycarbonylsulfanyl)propanoylamino]acetic acid (3)

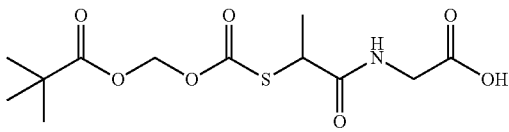 [SMILES: CC(SC(=O)OCOC(=O)C(C)(C)C)C(=O)NCC(=O)O]

Compound (3) was prepared according to the method described in Example 1 and substituting (2,5-dioxopyrrolidin-1-yl)oxycarbonyloxymethyl acetate with (2,5-dioxopyrrolidin-1-yl)oxycarbonyloxymethyl 2,2-dimethylpropanoate. MS (ESI): m/z 322.1 (M+H)+.

Example 4

2-[2-(Cyclohexanecarbonyloxymethoxycarbonylsulfanyl)propanoylamino]acetic acid (4)

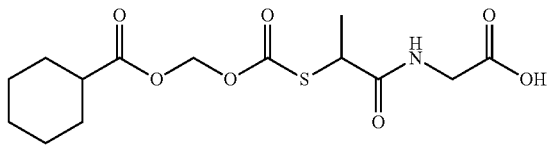 [SMILES: CC(SC(=O)OCOC(=O)C1CCCCC1)C(=O)NCC(=O)O]

Compound (4) was prepared according to the method described in Example 1 and substituting (2,5-dioxopyrrolidin-1-yl)oxycarbonyloxymethyl acetate with (2,5-dioxopyrrolidin-1-yl)oxycarbonyloxymethyl cyclohexanecarboxylate. MS (ESI): m/z 348.1 (M+H)+.

Example 5

2-[2-(Benzoyloxymethoxycarbonylsulfanyl)propanoylamino]acetic acid (5)

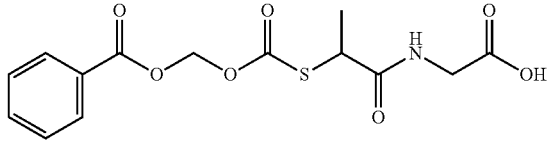 [SMILES: CC(SC(=O)OCOC(=O)c1ccccc1)C(=O)NCC(=O)O]

Compound (5) was prepared according to the method described in Example 1 and substituting (2,5-dioxopyrrolidin-1-yl)oxycarbonyloxymethyl acetate with (2,5-dioxopyrrolidin-1-yl)oxycarbonyloxymethyl benzoate. MS (ESI): m/z 342.1 (M+H)+.

Example 6

2-[2-[(5-Methyl-2-oxo-1,3-dioxol-4-yl)methoxycarbonylsulfanyl]propanoylamino]acetic acid (6)

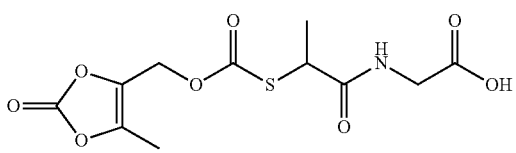 [SMILES: Cc1oc(=O)oc1COC(=O)SC(C)C(=O)NCC(=O)O]

Compound (6) was prepared according to the method described in Example 1 and substituting (2,5-dioxopyrrolidin-1-yl)oxycarbonyloxymethyl acetate with (5-methyl-2-oxo-1,3-dioxol-4-yl)methyl carbonochloridate. MS (ESI): m/z 320.0 (M+H)+.

Example 7

[2-[(2-Isopropoxy-2-oxo-ethyl)amino]-1-methyl-2-oxo-ethyl]sulfanylcarbonyloxymethyl 2-methylpropanoate (7)

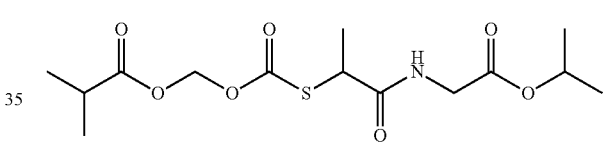

A mixture of thiolactic acid (0.50 g, 1.0 eq), (2,5-dioxopyrrolidin-1-yl)oxycarbonyloxymethyl 2-methylpropanoate (1.0 eq), and NaHCO$_3$ (or TEA) (2.0 eq) in ACN/water (or DMF) (5 mL) was stirred at 20° C. overnight. The reaction was concentrated in vacuo to a residue and then purified by reverse-phase (C-18) liquid chromatography using water and acetonitrile as eluents to yield compound (7a).

A mixture of compound (7a) (0.10 g, 1.0 eq), glycine isopropyl ester (1.0 eq), EDAC (1.5 eq), and DIEA (2.0 eq) in DCM (5 mL) was stirred at 20° C. overnight. The reaction was concentrated in vacuo to a residue and then purified by reverse-phase (C-18) liquid chromatography using water and acetonitrile as eluents to yield compound (7). MS (ESI): m/z 350.1 (M+H)+.

Example 8

[2-[(2-Benzyloxy-2-oxo-ethyl)amino]-1-methyl-2-oxo-ethyl]sulfanylcarbonyloxymethyl 2-methylpropanoate (8)

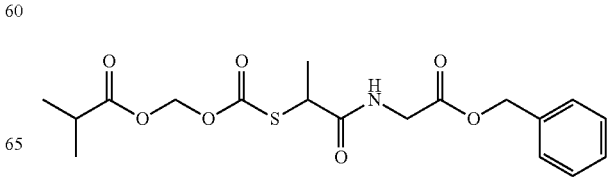

Compound (8) was prepared according to the method described in Example 7 and substituting glycine isopropyl ester with glycine benzyl ester. MS (ESI): m/z 398.1 (M+H)+.

Example 9

[2-[(2-Isopropoxy-2-oxo-ethyl)amino]-1-methyl-2-oxo-ethyl]sulfanylcarbonyloxymethyl benzoate (9)

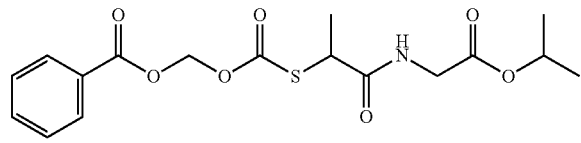 [SMILES: CC(C)OC(=O)CNC(=O)C(C)SC(=O)OCOC(=O)c1ccccc1]

Compound (9) was prepared according to the method described in Example 7 and substituting (2,5-dioxopyrrolidin-1-yl)oxycarbonyloxymethyl 2-methylpropanoate with (2,5-dioxopyrrolidin-1-yl)oxycarbonyloxymethyl benzoate. MS (ESI): m/z 384.1 (M+H)+.

Example 10

[2-[(2-Benzyloxy-2-oxo-ethyl)amino]-1-methyl-2-oxo-ethyl]sulfanylcarbonyloxymethyl benzoate (10)

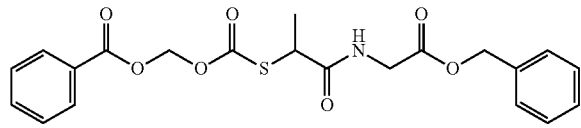 [SMILES: CC(SC(=O)OCOC(=O)c1ccccc1)C(=O)NCC(=O)OCc1ccccc1]

Compound (10) was prepared according to the method described in Example 7 and substituting glycine isopropyl ester with glycine benzyl ester and (2,5-dioxopyrrolidin-1-yl)oxycarbonyloxymethyl 2-methylpropanoate with (2,5-dioxopyrrolidin-1-yl)oxycarbonyloxymethyl benzoate. MS (ESI): m/z 432.1 (M+H)+.

Example 11

Isopropyl 2-[2-[(5-methyl-2-oxo-1,3-dioxol-4-yl)methoxycarbonylsulfanyl]propanoylamino]acetate (11)

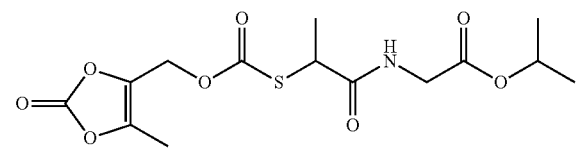 [SMILES: Cc1oc(=O)oc1COC(=O)SC(C)C(=O)NCC(=O)OC(C)C]

Compound (11) was prepared according to the method described in Example 7 and substituting (2,5-dioxopyrrolidin-1-yl)oxycarbonyloxymethyl 2-methylpropanoate with (5-methyl-2-oxo-1,3-dioxol-4-yl)methyl carbonochloridate. MS (ESI): m/z 362.1 (M+H)+.

Example 12

Benzyl 2-[2-[(5-methyl-2-oxo-1,3-dioxol-4-yl)methoxycarbonylsulfanyl]propanoylamino]acetate (12)

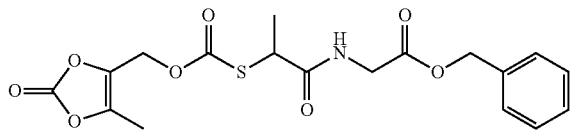 [SMILES: Cc1oc(=O)oc1COC(=O)SC(C)C(=O)NCC(=O)OCc1ccccc1]

Compound (12) was prepared according to the method described in Example 7 and substituting glycine isopropyl ester with glycine benzyl ester and (2,5-dioxopyrrolidin-1-yl)oxycarbonyloxymethyl 2-methylpropanoate with (5-methyl-2-oxo-1,3-dioxol-4-yl)methyl carbonochloridate. MS (ESI): m/z 410.1 (M+H)+.

The invention claimed is:
1. A compound according to Formula (I):

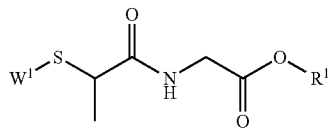

or a pharmaceutically acceptable salt thereof, wherein:
$R^1$ is chosen from hydrogen, $C_{1-6}$ alkyl, $C_{1-6}$ heteroalkyl, $C_{3-12}$ cycloalkyl, $C_{3-12}$ heterocycloalkyl, and $C_{5-10}$ aryl; and
$W^1$ is chosen from substituents of Formula (I-a) and Formula (I-b):

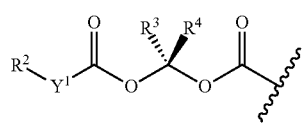

and

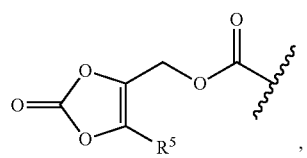

wherein
$R^2$, $R^3$, $R^4$, and $R^5$ are independently chosen from hydrogen, methyl, ethyl, n-propyl, isopropyl, n-butyl, isobutyl, tert-butyl, n-pentyl, pentyl-2-yl, 2-methylbutyl, isopentyl, 3-methylbutan-2-yl, neopentyl, tert-pentyl, n-hexyl, cyclohexyl, phenyl, and benzyl; and
$Y^1$ is chosen from a bond and —O—.

2. The compound according to claim 1, wherein $R^1$ is chosen from hydrogen, methyl, ethyl, n-propyl, isopropyl, tert-butyl, cyclohexyl, phenyl, benzyl, 2-morpholinoethyl, and 4-morpholinobutyl.

3. The compound according to claim 1, wherein $R^1$ is hydrogen.

4. The compound according to claim 1, wherein $W^1$ is chosen from the substituents of Formula (I-a) and Formula (I-b), wherein $R^2$, $R^3$, $R^4$, and $R^5$ are independently chosen from hydrogen, methyl, ethyl, isopropyl, tert-butyl, cyclohexyl, phenyl, and benzyl; and $Y^1$ is chosen from a bond and —O—.

5. The compound according to claim 1, wherein $W^1$ is chosen from the substituent of Formula (I-a), wherein $R^2$ is chosen from methyl, ethyl, isopropyl, tert-butyl, cyclohexyl, phenyl, and benzyl; $R^3$ and $R^4$ are hydrogen; and $Y^1$ is a bond.

6. The compound according to claim 1, wherein $W^1$ is chosen from the substituent of Formula (I-b), wherein $R^5$ is chosen from methyl, ethyl, isopropyl, tert-butyl, cyclohexyl, phenyl, and benzyl.

7. The compound according to claim 1, wherein $W^1$ is chosen from the substituent of Formula (I-b), wherein $R^5$ is methyl.

8. The compound according to claim 1, wherein $R^1$ is chosen from hydrogen, methyl, ethyl, n-propyl, isopropyl, tert-butyl, cyclohexyl, phenyl, benzyl, 2-morpholinoethyl, and 4-morpholinobutyl; and $W^1$ is chosen from the substituents of Formula (I-a) and Formula (I-b).

9. The compound according to claim 1, wherein $R^1$ is hydrogen; and $W^1$ is the substituent of Formula (I-a), wherein $R^2$ is methyl, $R^3$ and $R^4$ are hydrogen, and $Y^1$ is a bond.

10. The compound according to claim 1, wherein $R^1$ is hydrogen; and $W^1$ is the substituent of Formula (I-a), wherein $R^2$ is isopropyl, $R^3$ and $R^4$ are hydrogen, and $Y^1$ is a bond.

11. The compound according to claim 1, wherein $R^1$ is hydrogen; and $W^1$ is the substituent of Formula (I-a), wherein $R^2$ is phenyl, $R^3$ and $R^4$ are hydrogen, and $Y^1$ is a bond.

12. The compound according to claim 1, wherein $R^1$ is 2 morpholinoethyl; and $W^1$ is the substituent of Formula (I-a), wherein $R^2$ is isopropyl, $R^3$ and $R^4$ are hydrogen, and $Y^1$ is a bond.

13. The compound according to claim 1, wherein $R^1$ is hydrogen; and $W^1$ is the substituent of Formula (I-b), wherein $R^5$ is methyl.

14. The compound according to claim 1, wherein the compound is chosen from the compound of Formula (I-A-1), Formula (I-A-3), Formula (I-A-4), Formula (I-A-5), Formula (I-A-6), Formula (I-B-11), Formula (I-B-14), Formula (I-B-19), Formula (I-B-22), Formula (I-C-1), Formula (I-C-5), and Formula (I-C-8):

(I-A-1)

(I-A-3)

(I-A-4)

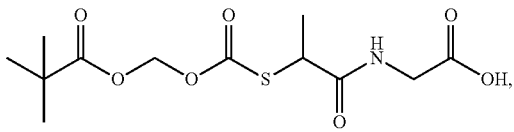

(I-A-5)

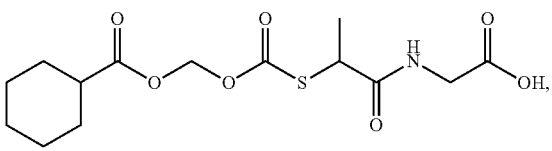

(I-A-6)

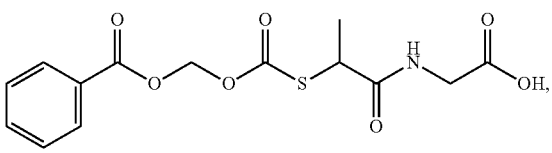

(I-B-11)

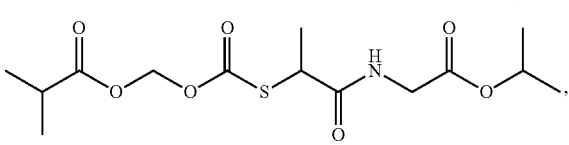

(I-B-14)

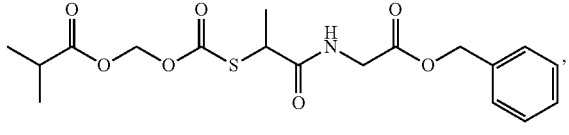

(I-B-19)

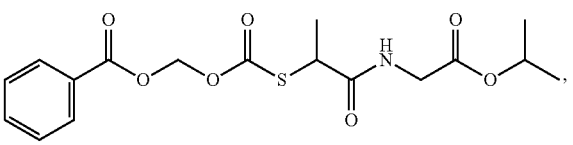

(I-B-22)

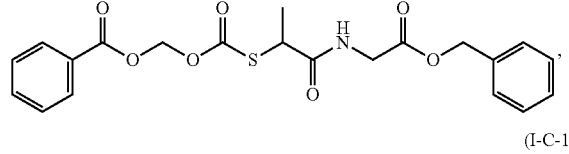

(I-C-1)

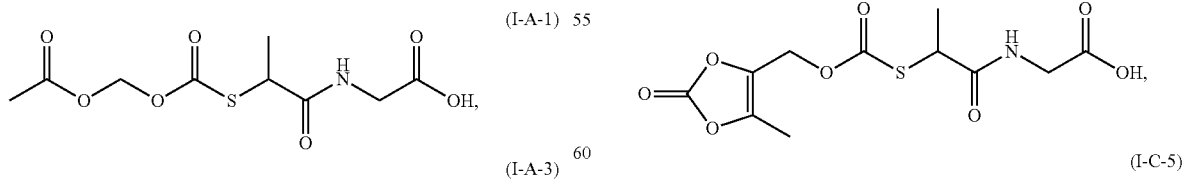

(I-C-5)

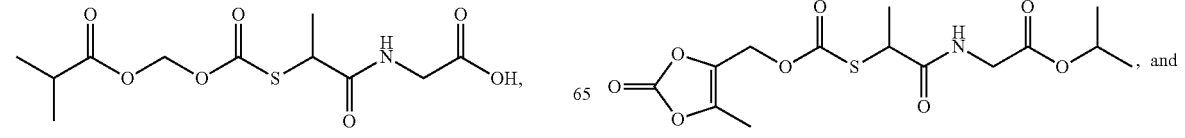

-continued (I-C-8)

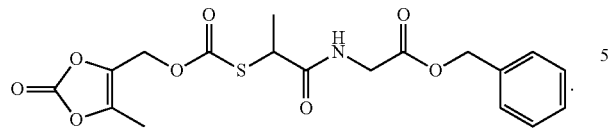

15. A pharmaceutical composition comprising a pharmaceutically acceptable vehicle and a therapeutically effective amount of a compound selected from the compounds listed in claim 14.

16. The pharmaceutical composition according to claim 15, wherein the composition is suitable for oral, inhalation, or topical administration.

17. The pharmaceutical composition according to claim 15, wherein the composition is suitable for controlled release formulation.

18. The pharmaceutical composition according to claim 15, wherein the composition is suitable for sustained release formulation.

* * * * *